United States Patent
Cleary

(10) Patent No.: US 6,270,775 B1
(45) Date of Patent: *Aug. 7, 2001

(54) STREPTOCOCCAL C5A PEPTIDASE VACCINE

(75) Inventor: Paul Patrick Cleary, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/206,800

(22) Filed: Dec. 7, 1998

Related U.S. Application Data

(62) Division of application No. 08/589,756, filed on Jan. 22, 1996, now Pat. No. 5,846,547.

(51) Int. Cl.$^7$ .......................... A61K 39/09; A61K 39/02; A61K 39/00; A61K 38/00; C12N 1/20

(52) U.S. Cl. .................... 424/244.1; 424/234.1; 424/184.1; 424/93; 424/177; 435/252.3; 514/2; 514/13

(58) Field of Search .................... 424/244.1, 234.1, 424/184.1, 93, 177; 435/252.3; 514/2, 13

(56) References Cited

U.S. PATENT DOCUMENTS

| | | | |
|---|---|---|---|
| 4,454,121 | 6/1984 | Beachey | 424/177 |
| 4,695,562 | 9/1987 | Beachey et al. | 514/13 |
| 4,772,584 | 9/1988 | Cleary et al. | 514/2 |
| 5,124,153 | 6/1992 | Beachy et al. | 424/93 P |
| 5,162,226 | 11/1992 | Beachey et al. | 435/252.3 |
| 5,846,547 | * 12/1998 | Cleary et al. | 424/244.1 |

FOREIGN PATENT DOCUMENTS

| | | | |
|---|---|---|---|
| 89/09064 | 10/1989 | (WO) . | |
| 93/14198 | 7/1993 | (WO) . | |
| 93/21220 | 10/1993 | (WO) . | |
| 94/06421 | 3/1994 | (WO) . | |
| 94/06465 | 3/1994 | (WO) . | |
| 95/28960 | 11/1995 | (WO) . | |
| 97/26008 | 1/1996 | (WO) | A61K/39/09 |

OTHER PUBLICATIONS

Brown protective immunity administered A Strept vaccines J. of Imm 141–2767–2770, 1988.*

Carter, P., et al., "Dissecting the catalytic triad of a serine protease", *Nature*, vol. 332, XP002135964, 564–568, (Apr. 7, 1988).

Stafslien, D.K., et al., "Site Directed Mutagenesis of the Streptococcal C5a Peptidase", *Abstracts of the General Mtg of the Am. Soc for Microbiology*, vol. 98, XP002135963, 59, (May, 1998).

Berg, A., et al., "Streptococcal Cysteine Proteinase Releases Biologically Active Fragments of Streptococcal Surface Proteins", *The Journal Of Biological Chemistry*, 270(17), 9862–9867, (1995).

Bessen, D., et al., "Influence of Intranasal Immunization with Synthetic Peptides Corresponding to Conserved Epitodes of M Protein on Mucosal Colonization by Group A Streptococci", *Infection and Immunity*, 56(10), 2666–2672, (1988).

Bessen, D., et al., "Synthetic Peptide Vaccine Against Mucusal Colonization by Group A Streptococci. I. Protection Against a Heterologous M Serotype with Shared C Repeat Region Epitopes", *J Immunol*, 145(4), 1251–1256, (1990).

Booth, S., et al., "Dapsone Suppresses Integrin–Mediated Neutrophil Adherence Function", *The Journal of Investigative Dermatology*, 98(2), 135–140, (1992).

Boyle, M., et al., "Measurement of Leukocyte Chemotaxis in Vivo", *Methods in Enzymology*, 162, 101–114, (1988).

Bronze, M., et al., "Epitopes of group A streptococcal M protein that evoke cross–protective local immune responses", *J. Immunol.*, 148(3), 888–893, (1992).

Bronze, M., et al., "Protective Immunity Evoked by Locally Administered Group A Streptcoccal Vaccines in Mice", *J. Immunol.*, 141(8), 2767–2770, (1988).

Brummer, E., et al., "Immunological Activation of Polymorphonuclear Neutrophilis for Fungal Killing: Studies with Murine Cells and Blastomyces Dermatitidis In Vitro", *Journal of Leukocyte Biology*, 36, 505–520, (1984).

Chen, C.C., et al., "Complete Nucleotide Sequence of the Streptococcal C5A Peptidase Gene of *Streptococcus pyogenes*", *The Journal of Bilogical Chemistry*, 265(6), 3161–3167, (1990).

Clark, J., et al., "A New Method for Quantitation of Cell–Mediated Immunity in the Mouse", *Journal of the Reticuloendothelial Society*, 25(3), 255–267, (1979).

Cleary, P., et al., "A Streptococcal Inactivator of Chemotaxis: A new Virulence Factor Specific to Group A Streptococci", *Recent Advances in Streptococci and Streptococcal Diseases* (Y. Kimura, S. Kotami and Y. Shiokawa (ed). Reedbooks ltd; Berkshire, England, 179–180, (1984).

(List continued on next page.)

*Primary Examiner*—Nita Minnifield
*Assistant Examiner*—Padma Baskar
(74) *Attorney, Agent, or Firm*—Schwegman, Lundberg, Woessner & Kluth, P.A.

(57) ABSTRACT

Novel vaccines for use against β-hemolytic Streptococcus colonization or infection are disclosed. The vaccines contain an immunogenic amount of streptococcal C5a peptidase, or a fragment or mutant thereof. Also disclosed is a method of protecting a susceptible mammal against β-hemolytic Streptococcus colonization or infection by administering such a vaccine.

42 Claims, 8 Drawing Sheets

OTHER PUBLICATIONS

Cleary, P., et al., "Similarity Between the Group B and A Streptococcal C5a Peptidase Genes", *Infection and Immunity*, 60(10), 4239–4244, (1992).

Cleary, P., et al., "Streptococcal C5a Peptidase is a Highly Specific Endopeptidase", *Infection and Immunity*, 60(12), 5219–5223, (1992).

Cleary, P., et al., "Virulent Human Strains of Group G Streptococci Express a C5a Peptidase Enzyme Similar to that Produced by Group A Streptococci", *Infection and Immunity*, 59(7), 2305–2310, (Jul. 1991).

Courtney, H.S., et al., "Analysis of the role of M24 Protein in group A Streptococcal adhesion and colonization by use of 'omega'–interposon mutagenesis", *Infect. Immun.*, 62(11), 4868–4873, (1994).

Fenderson, P., et al., "Tropomyosin Shares immunology Epitopes with Group A Streptococcal M Proteins", *The Journal of Immunology*, 142(7), 2475–2481, (Apr. 1989).

Fischetti, V., "Streptococcal M Protein: Molecular Design and Biological Behavior", *Clinical Microbiology Reviews*, 2(3), 285–314, (Jul. 1989).

Fischetti, V.A., et al., "Protection against streptoccal pharyngeal colonization with vaccines composed of M protein conserved regions", *Adv. Exp. Med. Bio.*, 303, 159–167, (1991).

Fischetti, V.A., et al., "Protection against streptococcal pharyngeal colinization with a vaccinia: M protein recombinant", *Science*, 244, 1487–1490, (1989).

Hill, H., et al., "Group B Streptococci Inhibit the Chemotactic Activity of the Fifth Component of Complement", *The Journal of Immunology*, 141(10), 3551–3556, (1988).

Hope–simpson, R., "Streptococcus Pyogenes in the Throat: A study in a small population, 1962–1975", *J. Hyg. Camb.*, 87, 109–129, (1981).

Ji, Y., et al., "C5a peptidase alters clearance and trafficking of group A streptococci by infected mice", *Infection and Immunity*, 64(2), 503–510, (1996).

Ji, Y., et al., "Intranasal immunization with C5a peptidase prevents nasopharyngeal colonization of mice by the group A streptococcus", *Infect. Immun.*, 65(6), 2080–2087, (1997).

Kapur, V., et al., "Vaccination with streptococcal extracellular cysteine protease (interleukin–1B convertase) protects mice against challenge with heterologous group A streptococci", *Microbial. Path.*, 16(6), 443–450, (1994).

Laemmli, U.K., "Cleavage of Structural Proteins during the Assembly of the Head of Bacteriophage T4", *Nature*, 227, 680–685 (1970).

Lee, P., et al., "Quantification and Toxicity of Group A Streptococcal Pyrogenic Exotoxins in an Animal Model of Toxic Shock Syndrome–Like Illness", *Journal of Clinical Microbiology*, 27(8), 1890–1892, (1989).

Martin, T., et al., "The Effect of Type–Specific Polysaccharide Capsule on the Clearance of Group B Sreptococci from the Lungs of Infant and Adult Rats", *The Journal of Infectious Diseases*, 165, 306–314, (1992).

Massell, B., et al., "Rheumatic Fever Following Streptococcal Vaccination", *JAMA*, 207(6), 1115–1119, (1969).

Mcghee, J., et al., "New Perspective in Mucosal Immunity with Emphasis on Vaccine Development", *Seminars in Hematology*, 30(4), 3–15, (1993).

Medaglini, D., et al., "Mucosal and systemic immune responses to a recombinant protein expressed on the surface of the oral commensal bacterium *Streptococcus gordonii* after oral colonization", *Proc. Natl. Acad. Sci. USA*, 92(15), 6868–6872, (1995).

O'connor, S., et al., "In Vivo Streptococcus Pyogenes C5a Peptidase Activity: Analysis Using Transposon– and Nitrosoguanidine– Induced Mutants", *The Journal of Infectious Diseases*, 156(3), 495–504, (1987).

O'connor, S., et al., "The Human Antibody Response to Streptococcal C5a Peptidase", *The Journal of Infection Diseases*, 163, 109–116, (1991).

Podbielski, A., et al., "The Group A Streptococcal VirR49 Gene Controls Expression of Four Structural Vir Regulon Genes", *Infection and Immunity*, 63(1), 9–20, (1995).

Raeder, R., et al., "Properties of IgG–binding proteins expressed by *Streptococcus pyogenes* isolates are predictive of invasive potential", *J. Infect. Dis.*, 173(4), 888–895, (1996).

Springer, T., et al., "Mac–1: A Macrophage Differentiation Antigen Identified by Monoclonal Antibody", *European Journal of Immunology*, 9, 301–306, (1979).

Sriskandan, S., et al., "Streptococcal pyrogenic exotoxin A (SPEA) release, distribution, and role in a murine model of fasciitis and multi–organ failure due to *Streptococcus pyogenes*", *J. Infect. Dis.*, 173(6), 1399–1407, (1996).

Sriskandan, S., et al., "The role of nitric oxide in experimental murine sepsis due to pyrogenic exotoxin A–producing *Streptococcus pyogenes*", *Infect. Immun.*, 65(5), 1767–1762, (1997).

Stevens, D., "Invasive Group A Streptococcus Infections", *Clinical Infectious Diseases*, 14, 2–13, (1992).

Suvorov, A., et al., "C5a Peptidase Gene from Group A Streptococci", *Genetics and Molecular Biology of Streptococci, Lactococci, and Enterococci*, Washington, D.C., 230–232, (1991).

Vugia, D.J., et al., "Invasive group A streptococcal infections in children with varicella in Southern California", *Pediatr. Infect. Dis. J.*, 15(2), 146–150, (1996).

Wessels, M., et al., "Critical role of the group A streptococcal capsule in pharyngeal colonization and infection in mice", *Proc. Natl. Acad. Sci. USA*, 91(25), 12238–12242, (1994).

Wexler, D., et al., "Mechanism of Action of the Group A Streptococcal C5a Inactivator", *Proc. Natl. Acad. Sci. 82*, 8144–8148, (1985).

\* cited by examiner

```
         1   LRKKQKLPFDKLAIALMSTSILLNAQSDIKANTVTEDTPATEQAVETPQPTTVSEEVPSS
                                  ▽
SCPA49   ---------------------------------------V-----------A-------
SCPA12   -----------------------------------------T-----------A----A-
SCPB

61  KETKTPQTPDDAEETVADDANDLAPQAPAKTPDTSATSKATIRDLNDPSQVKTLQEKAGK
             ----------------I------------------A-P----------------------
             ------S--G-------------------------A-P----------------------

121  GAGTVVAVIDAGFDKNHEAWRLTDKAKARYQSKEDLEKAKKEHGITYGEWVNDKVAYYHD
                 *                                T-------------------------
                                                  T-------------------------

181  YSKDGKTAVDQEHGTHVSGILSGNAPSETKEPYRLEGAMPEAQLLLMRVEIVNGLADYAR
                *

241  NYAQAIRDAVNLGAKVINMSFGNAALAYANLPDETKKPFVYAKSKGVRIVTTAGNDSSFG
             ----------------------------------A-D--------S-----S-------
             ------I---------------------------A-D--------S-----S-------

301  GKTRLPLADHPDYGVVGTPAAADSTLTTVASYSPDNQLTETAMVKTDDQQDKEMPVLSTNR
                                                   K-----------------------
                                                   K----------VR---A--------

361  FEPNKAYDYAYANRGMKEDDFKDVKGKIALIERSDIDFTDKIANAKKAGAVGVLIYDNQD
             ---------------------------------------------G----K--V-----
             ----T----------------------------------------G----K--K-----
```

FIG. 2A

```
421  KGFPIELPNVDQMPAAFISRKDGLLLKDNSQKTITFNATPKVLPTASGTKLSRFSSWGLT
     ---I--------------------------------------------------------
     ------------------------------------------------P-----------
     ------------------------------------------------P-----------
                    *
481  ADGNIKPDIAAPGQDILSSAANNKYAKLSGTSMSAPLVAVIMGLLQKQYETQYPDMTQSE
     -----------------V------------------------------------P-----
     -----------------V---------------------G--------------P-----
     -------------------------------------------------------P----
                                            G
541  RLDLAKKVLMSSATALYDEDEKAYFSPRQQGAGAVDAKKASEATMYVTDKDNTSSKVHLN
     ------------------------------------------A-----------------
     ------------------------------------------A-----------------
601  NVSDKFEVTVTVHNKSDKPHELYYQATVQTDKVDGKHFALAPKALIETSWQKITIPANSS
     -----------------------Q------------------------V-Y-A-------
     -----------------N-----Q------------------------V-Y-A-------
661  KQVTIPIDISQFSKDLLAQMKNGYFLEGFVRIKQDPTKEELMSIPYIGFRGDFGNLSALE
     ----V---A-R--------------------F----------------------------
     ----V---A-R--------------------F--------K-------------------V
721  KPLYDSKDGSSYYHEEISDAKDQLDGDGLQFYALKNDFTALTTESNPWTIINVVKEGVEN
     ---I------------AN-----------------N----------------------KA
     ---I------------AN-----------------N----------------------KA
781  IEDIESSEITETIFAGTFAKQDDDRHYYIHRHANGKPYAAISPNGDGNRDYVQFHGTFLR
     -------------------------S--------------------------E----Q--
     -----------L-------------S--------------------------------Q-
```

FIG. 2B

```
841  NAKNLVAEVLDKEGNVVWTSEVTEQVVKNYNNDLASTLGSTRFEISRWDGKDKDAKVVAN
     ----------------------------------------KT--------G---------
     ----------------------------------------KT--------G---------

901  GTYTYRVRYTPISSGAKEQHTDFDVIVDNTTPEVATSATFSTEDRRLTLASKPQTSQPVY
     ------------------------------------------------------K-----
     ------------------------------------------------------K-----

961  RERIAYTYMDEDLPTTEYISPNEDGTFTLPEEAETMEGATVPLKMSDFTYVVEDMAGNIT
     ------------------------------------------------------------
     ------------------------------------------------------------

1021 YTPVTKLLEGHSNKPEQDGSDQAPDKKPETKPEQDGSDQAPDKKPETKPGQDGSGQTPDK
     ------------------G-T------A-------T------A--E--------------
     ---------------------------------------------A--E-----------

1081 KPETKPEKDSSGQTPGKTPQKGQPSRTLEKRSSKRALATKASTRDQLPTTNDKDTNRLHL
     ------------------------------------------------------------
     ------------------------------------------------------------

1141 LKLVMTFFLGLVAHIFKTKR...TEDQKE-KK
     ----T---------F--------QKE-KK
     -----------------------QKE-KK
```

FIG. 2C

SEQUENCE LISTING

<160> NUMBER OF SEQ ID NOS: 11

<210> SEQ ID NO 1
<211> LENGTH: 1164
<212> TYPE: PRT
<213> ORGANISM: Streptococcus pyogenes, strain 49

<400> SEQUENCE: 1

```
Leu Arg Lys Lys Gln Lys Leu Pro Phe Asp Lys Leu Ala Ile Ala Leu
 1               5                  10                  15

Met Ser Thr Ser Ile Leu Leu Asn Ala Gln Ser Asp Ile Lys Ala Asn
            20                  25                  30

Thr Val Thr Glu Asp Thr Pro Ala Thr Glu Gln Ala Val Glu Thr Pro
        35                  40                  45

Gln Pro Thr Thr Val Ser Glu Glu Val Pro Ser Ser Lys Glu Thr Lys
    50                  55                  60

Thr Pro Gln Thr Pro Asp Asp Ala Glu Glu Thr Val Ala Asp Asp Ala
65                  70                  75                  80

Asn Asp Leu Ala Pro Gln Ala Pro Ala Lys Thr Pro Asp Thr Ser Ala
                85                  90                  95

Thr Ser Lys Ala Thr Ile Arg Asp Leu Asn Asp Pro Ser Gln Val Lys
            100                 105                 110

Thr Leu Gln Glu Lys Ala Gly Lys Gly Ala Gly Thr Val Val Ala Val
        115                 120                 125

Ile Asp Ala Gly Phe Asp Lys Asn His Glu Ala Trp Arg Leu Thr Asp
    130                 135                 140

Lys Ala Lys Ala Arg Tyr Gln Ser Lys Glu Asp Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Thr Ala Val Asp Gln Glu
            180                 185                 190

His Gly Thr His Val Ser Gly Ile Leu Ser Gly Asn Ala Pro Ser Glu
        195                 200                 205

Thr Lys Glu Pro Tyr Arg Leu Glu Gly Ala Met Pro Glu Ala Gln Leu
    210                 215                 220
```

-continued

```
Leu Leu Met Arg Val Glu Ile Val Asn Gly Leu Ala Asp Tyr Ala Arg
225                 230                 235                 240

Asn Tyr Ala Gln Ala Ile Arg Asp Ala Val Asn Leu Gly Ala Lys Val
                245                 250                 255

Ile Asn Met Ser Phe Gly Asn Ala Ala Leu Ala Tyr Ala Asn Leu Pro
                260                 265                 270

Asp Glu Thr Lys Lys Pro Phe Val Tyr Ala Lys Ser Lys Gly Val Arg
                275                 280                 285

Ile Val Thr Thr Ala Gly Asn Asp Ser Ser Phe Gly Gly Lys Thr Arg
290                 295                 300

Leu Pro Leu Ala Asp His Pro Asp Tyr Gly Val Val Gly Thr Pro Ala
305                 310                 315                 320

Ala Ala Asp Ser Thr Leu Thr Val Ala Ser Tyr Ser Pro Asp Asn Gln
                325                 330                 335

Leu Thr Glu Thr Ala Met Val Lys Thr Asp Asp Gln Gln Asp Lys Glu
                340                 345                 350

Met Pro Val Leu Ser Thr Asn Arg Phe Glu Pro Asn Lys Ala Tyr Asp
                355                 360                 365

Tyr Ala Tyr Ala Asn Arg Gly Met Lys Glu Asp Asp Phe Lys Asp Val
370                 375                 380

Lys Gly Lys Ile Ala Leu Ile Glu Arg Ser Asp Ile Asp Phe Thr Asp
385                 390                 395                 400

Lys Ile Ala Asn Ala Lys Lys Ala Gly Ala Val Gly Val Leu Ile Tyr
                405                 410                 415

Asp Asn Gln Asp Lys Gly Phe Pro Ile Glu Leu Pro Asn Val Asp Gln
                420                 425                 430

Met Pro Ala Ala Phe Ile Ser Arg Lys Asp Gly Leu Leu Leu Lys Asp
                435                 440                 445

Asn Ser Gln Lys Thr Ile Thr Phe Asn Ala Thr Pro Lys Val Leu Pro
                450                 455                 460

Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
                485                 490                 495

Leu Ser Ser Ala Ala Asn Asn Lys Tyr Ala Lys Leu Ser Gly Thr Ser
                500                 505                 510

Met Ser Ala Pro Leu Val Ala Val Ile Met Gly Leu Leu Gln Lys Gln
                515                 520                 525

Tyr Glu Thr Gln Tyr Pro Asp Met Thr Gln Ser Glu Arg Leu Asp Leu
                530                 535                 540

Ala Lys Lys Val Leu Met Ser Ser Ala Thr Ala Leu Tyr Asp Glu Asp
545                 550                 555                 560

Glu Lys Ala Tyr Phe Ser Pro Arg Gln Gln Gly Ala Gly Ala Val Asp
                565                 570                 575

Ala Lys Lys Ala Ser Glu Ala Thr Met Tyr Val Thr Asp Lys Asp Asn
                580                 585                 590

Thr Ser Ser Lys Val His Leu Asn Asn Val Ser Asp Lys Phe Glu Val
                595                 600                 605

Thr Val Thr Val His Asn Lys Ser Asp Lys Pro His Glu Leu Tyr Tyr
                610                 615                 620

Gln Ala Thr Val Gln Thr Asp Lys Val Asp Gly Lys His Phe Ala Leu
625                 630                 635                 640
```

```
Ala Pro Lys Ala Leu Ile Glu Thr Ser Trp Gln Lys Ile Thr Ile Pro
                645                 650                 655

Ala Asn Ser Ser Lys Gln Val Thr Ile Pro Ile Asp Ile Ser Gln Phe
            660                 665                 670

Ser Lys Asp Leu Leu Ala Gln Met Lys Asn Gly Tyr Phe Leu Glu Gly
        675                 680                 685

Phe Val Arg Ile Lys Gln Asp Pro Thr Lys Glu Leu Met Ser Ile
690                 695                 700

Pro Tyr Ile Gly Phe Arg Gly Asp Phe Gly Asn Leu Ser Ala Leu Glu
705                 710                 715                 720

Lys Pro Leu Tyr Asp Ser Lys Asp Gly Ser Ser Tyr His Glu
                725                 730                 735

Ile Ser Asp Ala Lys Asp Gln Leu Asp Gly Asp Gly Leu Gln Phe Tyr
                740                 745                 750

Ala Leu Lys Asn Asp Phe Thr Ala Leu Thr Thr Glu Ser Asn Pro Trp
            755                 760                 765

Thr Ile Ile Asn Val Val Lys Glu Gly Val Glu Asn Ile Glu Asp Ile
    770                 775                 780

Glu Ser Ser Glu Ile Thr Glu Thr Ile Phe Ala Gly Thr Phe Ala Lys
785                 790                 795                 800

Gln Asp Asp Asp Arg His Tyr Tyr Ile His Arg His Ala Asn Gly Lys
                805                 810                 815

Pro Tyr Ala Ala Ile Ser Pro Asn Gly Asp Gly Asn Arg Asp Tyr Val
                820                 825                 830

Gln Phe His Gly Thr Phe Leu Arg Asn Ala Lys Asn Leu Val Ala Glu
        835                 840                 845

Val Leu Asp Lys Glu Gly Asn Val Val Trp Thr Ser Glu Val Thr Glu
    850                 855                 860

Gln Val Val Lys Asn Tyr Asn Asn Asp Leu Ala Ser Thr Leu Gly Ser
865                 870                 875                 880

Thr Arg Phe Glu Ile Ser Arg Trp Asp Gly Lys Asp Lys Asp Ala Lys
                885                 890                 895

Val Val Ala Asn Gly Thr Tyr Thr Tyr Arg Val Arg Tyr Thr Pro Ile
                900                 905                 910

Ser Ser Gly Ala Lys Glu Gln His Thr Asp Phe Asp Val Ile Val Asp
            915                 920                 925

Asn Thr Thr Pro Glu Val Ala Thr Ser Ala Thr Phe Ser Thr Glu Asp
    930                 935                 940

Arg Arg Leu Thr Leu Ala Ser Lys Pro Gln Thr Ser Gln Pro Val Tyr
945                 950                 955                 960

Arg Glu Arg Ile Ala Tyr Thr Tyr Met Asp Glu Asp Leu Pro Thr Thr
                965                 970                 975

Glu Tyr Ile Ser Pro Asn Glu Asp Gly Thr Phe Thr Leu Pro Glu Glu
            980                 985                 990

Ala Glu Thr Met Glu Gly Ala Thr Val Pro Leu Lys Met Ser Asp Phe
        995                 1000                1005

Thr Tyr Val Val Glu Asp Met Ala Gly Asn Ile Thr Tyr Thr Pro Val
        1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Thr Lys Pro Glu Gln Asp Gly
                1045                1050                1055
```

-continued

```
Ser Asp Gln Ala Pro Asp Lys Lys Pro Glu Thr Lys Pro Gly Gln Asp
        1060                1065                1070

Gly Ser Gly Gln Thr Pro Asp Lys Lys Pro Glu Thr Lys Pro Glu Lys
        1075                1080                1085

Asp Ser Ser Gly Gln Thr Pro Gly Lys Thr Pro Gln Lys Gly Gln Pro
        1090                1095                1100

Ser Arg Thr Leu Glu Lys Arg Ser Ser Lys Arg Ala Leu Ala Thr Lys
1105                1110                1115                1120

Ala Ser Thr Arg Asp Gln Leu Pro Thr Thr Asn Asp Lys Asp Thr Asn
                1125                1130                1135

Arg Leu His Leu Leu Lys Leu Val Met Thr Thr Phe Phe Leu Gly Leu
                1140                1145                1150

Val Ala His Ile Phe Lys Thr Lys Arg Thr Glu Asp
                1155                1160

<210> SEQ ID NO 2
<211> LENGTH: 1167
<212> TYPE: PRT
<213> ORGANISM: Streptococcus pyogenes, strain 12

<400> SEQUENCE: 2

Leu Arg Lys Lys Gln Lys Leu Pro Phe Asp Lys Leu Ala Ile Ala Leu
 1               5                  10                  15

Met Ser Thr Ser Ile Leu Leu Asn Ala Gln Ser Asp Ile Lys Ala Asn
                20                  25                  30

Thr Val Thr Glu Asp Thr Pro Val Thr Glu Gln Ala Val Glu Thr Pro
            35                  40                  45

Gln Pro Thr Ala Val Ser Glu Glu Val Pro Ser Ser Lys Glu Thr Lys
    50                  55                  60

Thr Pro Gln Thr Pro Asp Asp Ala Glu Glu Thr Ile Ala Asp Asp Ala
65                  70                  75                  80

Asn Asp Leu Ala Pro Gln Ala Pro Ala Lys Thr Ala Asp Thr Pro Ala
                85                  90                  95

Thr Ser Lys Ala Thr Ile Arg Asp Leu Asn Asp Pro Ser Gln Val Lys
                100                 105                 110

Thr Leu Gln Glu Lys Ala Gly Lys Gly Ala Gly Thr Val Val Ala Val
            115                 120                 125

Ile Asp Ala Gly Phe Asp Lys Asn His Glu Ala Trp Arg Leu Thr Asp
130                 135                 140

Lys Thr Lys Ala Arg Tyr Gln Ser Lys Glu Asp Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Thr Ala Val Asp Gln Glu
                180                 185                 190

His Gly Thr His Val Ser Gly Ile Leu Ser Gly Asn Ala Pro Ser Glu
            195                 200                 205

Thr Lys Glu Pro Tyr Arg Leu Glu Gly Ala Met Pro Glu Ala Gln Leu
    210                 215                 220

Leu Leu Met Arg Val Glu Ile Val Asn Gly Leu Ala Asp Tyr Ala Arg
225                 230                 235                 240

Asn Tyr Ala Gln Ala Ile Arg Asp Ala Val Asn Leu Gly Ala Lys Val
                245                 250                 255

Ile Asn Met Ser Phe Gly Asn Ala Ala Leu Ala Tyr Ala Asn Leu Pro
                260                 265                 270
```

-continued

```
Asp Glu Thr Lys Lys Ala Phe Asp Tyr Ala Lys Ser Lys Gly Val Ser
        275                 280                 285

Ile Val Thr Ser Ala Gly Asn Asp Ser Ser Phe Gly Gly Lys Thr Arg
        290                 295                 300

Leu Pro Leu Ala Asp His Pro Asp Tyr Gly Val Val Gly Thr Pro Ala
305                 310                 315                 320

Ala Ala Asp Ser Thr Leu Thr Val Ala Ser Tyr Ser Pro Asp Lys Gln
                325                 330                 335

Leu Thr Glu Thr Ala Met Val Lys Thr Asp Gln Gln Asp Lys Glu
                340                 345                 350

Met Pro Val Leu Ser Thr Asn Arg Phe Glu Pro Asn Lys Ala Tyr Asp
                355                 360                 365

Tyr Ala Tyr Ala Asn Arg Gly Met Lys Glu Asp Asp Phe Lys Asp Val
        370                 375                 380

Lys Gly Lys Ile Ala Leu Ile Glu Arg Gly Asp Ile Asp Phe Lys Asp
385                 390                 395                 400

Lys Val Ala Asn Ala Lys Lys Ala Gly Ala Val Gly Val Leu Ile Tyr
                405                 410                 415

Asp Asn Gln Asp Lys Gly Phe Pro Ile Glu Leu Pro Asn Val Asp Gln
                420                 425                 430

Met Pro Ala Ala Phe Ile Ser Arg Lys Asp Gly Leu Leu Leu Lys Asp
        435                 440                 445

Asn Pro Gln Lys Thr Ile Thr Phe Asn Ala Thr Pro Lys Val Leu Pro
450                 455                 460

Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
                485                 490                 495

Leu Ser Ser Val Ala Asn Asn Lys Tyr Ala Lys Leu Ser Gly Thr Ser
                500                 505                 510

Met Ser Ala Pro Leu Val Ala Gly Ile Met Gly Leu Leu Gln Lys Gln
                515                 520                 525

Tyr Glu Thr Gln Tyr Pro Asp Met Thr Pro Ser Glu Arg Leu Asp Leu
                530                 535                 540

Ala Lys Lys Val Leu Met Ser Ser Ala Thr Ala Leu Tyr Asp Glu Asp
545                 550                 555                 560

Glu Lys Ala Tyr Phe Ser Pro Arg Gln Gln Gly Ala Gly Ala Val Asp
                565                 570                 575

Ala Lys Lys Ala Ser Ala Ala Thr Met Tyr Val Thr Asp Lys Asp Asn
                580                 585                 590

Thr Ser Ser Lys Val His Leu Asn Asn Val Ser Asp Lys Phe Glu Val
                595                 600                 605

Thr Val Thr Val His Asn Lys Ser Asp Lys Pro Gln Glu Leu Tyr Tyr
        610                 615                 620

Gln Ala Thr Val Gln Thr Asp Lys Val Asp Gly Lys His Phe Ala Leu
625                 630                 635                 640

Ala Pro Lys Val Leu Tyr Glu Ala Ser Trp Gln Lys Ile Thr Ile Pro
                645                 650                 655

Ala Asn Ser Ser Lys Gln Val Thr Val Pro Ile Asp Ala Ser Arg Phe
                660                 665                 670

Ser Lys Asp Leu Leu Ala Gln Met Lys Asn Gly Tyr Phe Leu Glu Gly
        675                 680                 685
```

-continued

```
Phe Val Arg Phe Lys Gln Asp Pro Thr Lys Glu Glu Leu Met Ser Ile
690                 695                 700
Pro Tyr Ile Gly Phe Arg Gly Asp Phe Gly Asn Leu Ser Ala Val Glu
705                 710                 715                 720
Lys Pro Ile Tyr Asp Ser Lys Asp Gly Ser Ser Tyr Tyr His Glu Ala
                725                 730                 735
Asn Ser Asp Ala Lys Asp Gln Leu Asp Gly Asp Gly Leu Gln Phe Tyr
                740                 745                 750
Ala Leu Lys Asn Asn Phe Thr Ala Leu Thr Thr Glu Ser Asn Pro Trp
                755                 760                 765
Thr Ile Ile Lys Ala Val Lys Glu Gly Val Glu Asn Ile Glu Asp Ile
                770                 775                 780
Glu Ser Ser Glu Ile Thr Glu Thr Ile Phe Ala Gly Thr Phe Ala Lys
785                 790                 795                 800
Gln Asp Asp Asp Ser His Tyr Tyr Ile His Arg His Ala Asn Gly Glu
                805                 810                 815
Pro Tyr Ala Ala Ile Ser Pro Asn Gly Asp Gly Asn Arg Asp Tyr Val
                820                 825                 830
Gln Phe Gln Gly Thr Phe Leu Arg Asn Ala Lys Asn Leu Val Ala Glu
                835                 840                 845
Val Leu Asp Lys Glu Gly Asn Val Val Trp Thr Ser Glu Val Thr Glu
                850                 855                 860
Gln Val Val Lys Asn Tyr Asn Asn Asp Leu Ala Ser Thr Leu Gly Ser
865                 870                 875                 880
Thr Arg Phe Glu Lys Thr Arg Trp Asp Gly Lys Asp Lys Asp Gly Lys
                885                 890                 895
Val Val Ala Asn Gly Thr Tyr Thr Tyr Arg Val Arg Tyr Thr Pro Ile
                900                 905                 910
Ser Ser Gly Ala Lys Glu Gln His Thr Asp Phe Asp Val Ile Val Asp
                915                 920                 925
Asn Thr Thr Pro Glu Val Ala Thr Ser Ala Thr Phe Ser Thr Glu Asp
                930                 935                 940
Arg Arg Leu Thr Leu Ala Ser Lys Pro Lys Thr Ser Gln Pro Val Tyr
945                 950                 955                 960
Arg Glu Arg Ile Ala Tyr Thr Tyr Met Asp Glu Asp Leu Pro Thr Thr
                965                 970                 975
Glu Tyr Ile Ser Pro Asn Glu Asp Gly Thr Phe Thr Leu Pro Glu Glu
                980                 985                 990
Ala Glu Thr Met Glu Gly Ala Thr Val Pro Leu Lys Met Ser Asp Phe
                995                 1000                1005
Thr Tyr Val Val Glu Asp Met Ala Gly Asn Ile Thr Tyr Thr Pro Val
                1010                1015                1020
Thr Lys Leu Leu Glu Gly His Ser Asn Lys Pro Glu Gln Asp Gly Ser
1025                1030                1035                1040
Gly Gln Thr Pro Asp Lys Lys Pro Glu Ala Lys Pro Glu Gln Asp Gly
                1045                1050                1055
Ser Asp Gln Ala Pro Asp Lys Lys Pro Glu Ala Lys Pro Glu Gln Asp
                1060                1065                1070
Gly Ser Gly Gln Thr Pro Asp Lys Lys Pro Glu Thr Lys Pro Glu Lys
                1075                1080                1085
Asp Ser Ser Gly Gln Thr Pro Gly Lys Thr Pro Gln Lys Gly Gln Pro
                1090                1095                1100
```

```
Ser Arg Thr Leu Glu Lys Arg Ser Lys Arg Ala Leu Ala Thr Lys
1105                1110                1115                1120

Ala Ser Thr Arg Asp Gln Leu Pro Thr Asn Asp Lys Asp Thr Asn
            1125                1130                1135

Arg Leu His Leu Leu Lys Leu Val Met Thr Thr Phe Phe Gly Leu
            1140                1145                1150

Val Ala His Ile Phe Lys Thr Lys Arg Gln Lys Glu Thr Lys Lys
            1155                1160                1165

<210> SEQ ID NO 3
<211> LENGTH: 1150
<212> TYPE: PRT
<213> ORGANISM: Streptococcus agalactiae

<400> SEQUENCE: 3

Leu Arg Lys Lys Gln Lys Leu Pro Phe Asp Lys Leu Ala Ile Ala Leu
 1               5                  10                  15

Met Ser Thr Ser Ile Leu Leu Asn Ala Gln Ser Asp Ile Lys Ala Asn
                20                  25                  30

Thr Val Thr Glu Asp Thr Pro Ala Thr Glu Gln Thr Val Glu Thr Pro
            35                  40                  45

Gln Pro Thr Ala Val Ser Glu Glu Ala Pro Ser Ser Lys Glu Thr Lys
    50                  55                  60

Thr Pro Gln Thr Pro Ser Asp Ala Gly Glu Thr Val Ala Asp Asp Ala
65                  70                  75                  80

Asn Asp Leu Ala Pro Gln Ala Pro Ala Lys Thr Ala Asp Thr Pro Ala
                85                  90                  95

Thr Ser Lys Ala Thr Ile Arg Asp Leu Asn Asp Pro Ser Gln Val Lys
            100                 105                 110

Thr Leu Gln Glu Lys Ala Gly Lys Gly Ala Gly Thr Val Val Ala Val
        115                 120                 125

Ile Asp Ala Gly Phe Asp Lys Asn His Glu Ala Trp Arg Leu Thr Asp
130                 135                 140

Lys Thr Lys Ala Arg Tyr Gln Ser Lys Glu Asp Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Thr Ala Val Asp Gln Glu
            180                 185                 190

His Gly Thr His Val Ser Gly Ile Leu Ser Gly Asn Ala Pro Ser Glu
        195                 200                 205

Thr Lys Glu Pro Tyr Arg Leu Glu Gly Ala Met Pro Glu Ala Gln Leu
    210                 215                 220

Leu Leu Met Arg Val Glu Ile Val Asn Gly Leu Ala Asp Tyr Ala Arg
225                 230                 235                 240

Asn Tyr Ala Gln Ala Ile Arg Asp Ala Ile Asn Leu Gly Ala Lys Val
                245                 250                 255

Ile Asn Met Ser Phe Gly Asn Ala Ala Leu Ala Tyr Ala Asn Leu Pro
            260                 265                 270

Asp Glu Thr Lys Lys Ala Phe Asp Tyr Ala Lys Ser Lys Gly Val Ser
        275                 280                 285

Ile Val Thr Ser Ala Gly Asn Asp Ser Ser Phe Gly Gly Lys Thr Arg
    290                 295                 300

Leu Pro Leu Ala Asp His Pro Asp Tyr Gly Val Val Gly Thr Pro Ala
305                 310                 315                 320
```

```
Ala Ala Asp Ser Thr Leu Thr Val Ala Ser Tyr Ser Pro Asp Lys Gln
            325                 330                 335

Leu Thr Glu Thr Val Arg Val Lys Thr Ala Asp Gln Gln Asp Lys Glu
            340                 345                 350

Met Pro Val Leu Ser Thr Asn Arg Phe Glu Pro Asn Lys Ala Tyr Asp
            355                 360                 365

Tyr Ala Tyr Ala Asn Arg Gly Thr Lys Glu Asp Phe Lys Asp Val
        370                 375                 380

Lys Gly Lys Ile Ala Leu Ile Glu Arg Gly Asp Ile Asp Phe Lys Asp
385                 390                 395                 400

Lys Ile Ala Lys Ala Lys Lys Ala Gly Ala Val Gly Val Leu Ile Tyr
                405                 410                 415

Asp Asn Gln Asp Lys Gly Phe Pro Ile Glu Leu Pro Asn Val Asp Gln
                420                 425                 430

Met Pro Ala Ala Phe Ile Ser Arg Lys Asp Gly Leu Leu Lys Asp
            435                 440                 445

Asn Pro Gln Lys Thr Ile Thr Phe Asn Ala Thr Pro Lys Val Leu Pro
450                 455                 460

Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
                485                 490                 495

Leu Ser Ser Val Ala Asn Asn Lys Tyr Ala Lys Leu Ser Gly Thr Ser
                500                 505                 510

Met Ser Ala Pro Leu Val Ala Gly Ile Met Gly Leu Leu Gln Lys Gln
            515                 520                 525

Tyr Glu Thr Gln Tyr Pro Asp Met Thr Pro Ser Glu Arg Leu Asp Leu
            530                 535                 540

Ala Lys Lys Val Leu Met Ser Ser Ala Thr Ala Leu Tyr Asp Glu Asp
545                 550                 555                 560

Glu Lys Ala Tyr Phe Ser Pro Arg Gln Gln Gly Ala Gly Ala Val Asp
                565                 570                 575

Ala Lys Lys Ala Ser Ala Ala Thr Met Tyr Val Thr Asp Lys Asp Asn
            580                 585                 590

Thr Ser Ser Lys Val His Leu Asn Asn Val Ser Asp Lys Phe Glu Val
            595                 600                 605

Thr Val Asn Val His Asn Lys Ser Asp Lys Pro Gln Glu Leu Tyr Tyr
            610                 615                 620

Gln Ala Thr Val Gln Thr Asp Lys Val Asp Gly Lys His Phe Ala Leu
625                 630                 635                 640

Ala Pro Lys Val Leu Tyr Glu Ala Ser Trp Gln Lys Ile Thr Ile Pro
                645                 650                 655

Ala Asn Ser Ser Lys Gln Val Thr Val Pro Ile Asp Ala Ser Arg Phe
                660                 665                 670

Ser Lys Asp Leu Leu Ala Gln Met Lys Asn Gly Tyr Phe Leu Glu Gly
            675                 680                 685

Phe Val Arg Phe Lys Gln Asp Pro Lys Lys Glu Glu Leu Met Ser Ile
            690                 695                 700

Pro Tyr Ile Gly Phe Arg Gly Asp Phe Gly Asn Leu Ser Ala Leu Glu
705                 710                 715                 720

Lys Pro Ile Tyr Asp Ser Lys Asp Gly Ser Ser Tyr Tyr His Glu Ala
                725                 730                 735
```

-continued

```
Asn Ser Asp Ala Lys Asp Gln Leu Asp Gly Asp Gly Leu Gln Phe Tyr
            740                 745                 750

Ala Leu Lys Asn Asn Phe Thr Ala Leu Thr Thr Glu Ser Asn Pro Trp
            755                 760                 765

Thr Ile Ile Lys Ala Val Lys Glu Gly Val Glu Asn Ile Glu Asp Ile
            770                 775                 780

Glu Ser Ser Glu Ile Thr Glu Thr Ile Leu Ala Gly Thr Phe Ala Lys
785                 790                 795                 800

Gln Asp Asp Ser His Tyr Tyr Ile His Arg His Ala Asn Gly Lys
            805                 810                 815

Pro Tyr Ala Ala Ile Ser Pro Asn Gly Asp Gly Asn Arg Asp Tyr Val
            820                 825                 830

Gln Phe Gln Gly Thr Phe Leu Arg Asn Ala Lys Asn Leu Val Ala Glu
            835                 840                 845

Val Leu Asp Lys Glu Gly Asn Val Val Trp Thr Ser Glu Val Thr Glu
            850                 855                 860

Gln Val Val Lys Asn Tyr Asn Asn Asp Leu Ala Ser Thr Leu Gly Ser
865                 870                 875                 880

Thr Arg Phe Glu Lys Thr Arg Trp Asp Gly Lys Asp Lys Asp Gly Lys
            885                 890                 895

Val Val Ala Asn Gly Thr Tyr Thr Tyr Arg Val Arg Tyr Thr Pro Ile
            900                 905                 910

Ser Ser Gly Ala Lys Glu Gln His Thr Asp Phe Asp Val Ile Val Asp
            915                 920                 925

Asn Thr Thr Pro Glu Val Ala Thr Ser Ala Thr Phe Ser Thr Glu Asp
            930                 935                 940

Arg Arg Leu Thr Leu Ala Ser Lys Pro Lys Thr Ser Gln Pro Val Tyr
945                 950                 955                 960

Arg Glu Arg Ile Ala Tyr Thr Tyr Met Asp Glu Asp Leu Pro Thr Thr
            965                 970                 975

Glu Tyr Ile Ser Pro Asn Glu Asp Gly Thr Phe Thr Leu Pro Glu Glu
            980                 985                 990

Ala Glu Thr Thr Glu Gly Ala Thr Val Pro Leu Lys Met Ser Asp Phe
            995                 1000                1005

Thr Tyr Val Val Glu Asp Met Ala Gly Asn Ile Thr Tyr Thr Pro Val
            1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Ala Lys Pro Glu Gln Asp Gly
            1045                1050                1055

Ser Gly Gln Thr Pro Asp Lys Lys Thr Glu Thr Lys Pro Glu Lys Asp
            1060                1065                1070

Ser Ser Gly Gln Thr Pro Gly Lys Thr Pro Gln Lys Gly Gln Pro Ser
            1075                1080                1085

Arg Thr Leu Glu Lys Arg Ser Ser Lys Arg Ala Leu Ala Thr Lys Ala
            1090                1095                1100

Ser Thr Arg Asp Gln Leu Pro Thr Thr Asn Asp Lys Asp Thr Asn Arg
1105                1110                1115                1120

Leu His Leu Leu Lys Leu Val Met Thr Thr Phe Phe Leu Gly Leu Val
            1125                1130                1135

Ala His Ile Phe Lys Thr Lys Arg Gln Lys Glu Thr Lys Lys
            1140                1145                1150
```

```
<210> SEQ ID NO 4
<211> LENGTH: 31
<212> TYPE: DNA
<213> ORGANISM: Artificial Sequence
<220> FEATURE:
<223> OTHER INFORMATION: A primer

<400> SEQUENCE: 4 ggggggggaat tcgtagcggg tatcatggga c                          31

<210> SEQ ID NO 5
<211> LENGTH: 31
<212> TYPE: DNA
<213> ORGANISM: Artificial Sequence
<220> FEATURE:
<223> OTHER INFORMATION: A primer

<400> SEQUENCE: 5 ggggggggaat tcgggtgctg caatatctgg c                          31

<210> SEQ ID NO 6
<211> LENGTH: 383
<212> TYPE: PRT
<213> ORGANISM: Streptococcus pyogenes, strain 49

<400> SEQUENCE: 6
```

| | | | | | | | | | | | | | | | |
|---|---|---|---|---|---|---|---|---|---|---|---|---|---|---|---|
| Asp | Ala | Gly | Phe | Asp | Lys | Asn | His | Glu | Ala | Trp | Arg | Leu | Thr | Asp | Lys |
| 1 | | | | 5 | | | | | 10 | | | | | 15 | |
| Ala | Lys | Ala | Arg | Tyr | Gln | Ser | Lys | Glu | Asp | Leu | Glu | Lys | Ala | Lys | Lys |
| | | | 20 | | | | | 25 | | | | | 30 | | |
| Glu | His | Gly | Ile | Thr | Tyr | Gly | Glu | Trp | Val | Asn | Asp | Lys | Val | Ala | Tyr |
| | | | | 35 | | | | | 40 | | | | | 45 | |
| Tyr | His | Asp | Tyr | Ser | Lys | Asp | Gly | Lys | Thr | Ala | Val | Asp | Gln | Glu | His |
| 50 | | | | | 55 | | | | | 60 | | | | | |
| Gly | Thr | His | Val | Ser | Gly | Ile | Leu | Ser | Gly | Asn | Ala | Pro | Ser | Glu | Thr |
| 65 | | | | | 70 | | | | | 75 | | | | | 80 |
| Lys | Glu | Pro | Tyr | Arg | Leu | Glu | Gly | Ala | Met | Pro | Glu | Ala | Gln | Leu | Leu |
| | | | | 85 | | | | | 90 | | | | | 95 | |
| Leu | Met | Arg | Val | Glu | Ile | Val | Asn | Gly | Leu | Ala | Asp | Tyr | Ala | Arg | Asn |
| | | | | 100 | | | | | 105 | | | | | 110 | |
| Tyr | Ala | Gln | Ala | Ile | Arg | Asp | Ala | Val | Asn | Leu | Gly | Ala | Lys | Val | Ile |
| | | | 115 | | | | | 120 | | | | | 125 | | |
| Asn | Met | Ser | Phe | Gly | Asn | Ala | Ala | Leu | Ala | Tyr | Ala | Asn | Leu | Pro | Asp |
| | | 130 | | | | | 135 | | | | | 140 | | | |
| Glu | Thr | Lys | Lys | Pro | Phe | Val | Tyr | Ala | Lys | Ser | Lys | Gly | Val | Arg | Ile |
| 145 | | | | | 150 | | | | | 155 | | | | | 160 |
| Val | Thr | Thr | Ala | Gly | Asn | Asp | Ser | Ser | Phe | Gly | Gly | Lys | Thr | Arg | Leu |
| | | | | 165 | | | | | 170 | | | | | 175 | |
| Pro | Leu | Ala | Asp | His | Pro | Asp | Tyr | Gly | Val | Val | Gly | Thr | Pro | Ala | Ala |
| | | | 180 | | | | | 185 | | | | | 190 | | |
| Ala | Asp | Ser | Thr | Leu | Thr | Val | Ala | Ser | Tyr | Ser | Pro | Asp | Asn | Gln | Leu |
| | | | 195 | | | | | 200 | | | | | 205 | | |
| Thr | Glu | Thr | Ala | Met | Val | Lys | Thr | Asp | Gln | Gln | Asp | Lys | Glu | Met |
| | 210 | | | | | 215 | | | | | 220 | | | | |
| Pro | Val | Leu | Ser | Thr | Asn | Arg | Phe | Glu | Pro | Asn | Lys | Ala | Tyr | Asp | Tyr |
| 225 | | | | | 230 | | | | | 235 | | | | | 240 |
| Ala | Tyr | Ala | Asn | Arg | Gly | Met | Lys | Glu | Asp | Asp | Phe | Lys | Asp | Val | Lys |
| | | | | 245 | | | | | 250 | | | | | 255 | |

```
Gly Lys Ile Ala Leu Ile Glu Arg Ser Asp Ile Asp Phe Thr Asp Lys
            260                 265                 270

Ile Ala Asn Ala Lys Lys Ala Gly Ala Val Gly Val Leu Ile Tyr Asp
            275                 280                 285

Asn Gln Asp Lys Gly Phe Pro Ile Glu Leu Pro Asn Val Asp Gln Met
            290                 295                 300

Pro Ala Ala Phe Ile Ser Arg Lys Asp Gly Leu Leu Leu Lys Asp Asn
305                 310                 315                 320

Ser Gln Lys Thr Ile Thr Phe Asn Ala Thr Pro Lys Val Leu Pro Thr
                    325                 330                 335

Ala Ser Gly Thr Lys Leu Ser Arg Phe Ser Ser Trp Gly Leu Thr Ala
                340                 345                 350

Asp Gly Asn Ile Lys Pro Asp Ile Ala Ala Pro Gly Gln Asp Ile Leu
            355                 360                 365

Ser Ser Ala Ala Asn Asn Lys Tyr Ala Lys Leu Ser Gly Thr Ser
            370                 375                 380

<210> SEQ ID NO 7
<211> LENGTH: 383
<212> TYPE: PRT
<213> ORGANISM: Streptococcus pyogenes, strain 12

<400> SEQUENCE: 7

Asp Ala Gly Phe Asp Lys Asn His Glu Ala Trp Arg Leu Thr Asp Lys
1               5                   10                  15

Thr Lys Ala Arg Tyr Gln Ser Lys Glu Asp Leu Glu Lys Ala Lys Lys
                20                  25                  30

Glu His Gly Ile Thr Tyr Gly Glu Trp Val Asn Asp Lys Val Ala Tyr
            35                  40                  45

Tyr His Asp Tyr Ser Lys Asp Gly Lys Thr Ala Val Asp Gln Glu His
    50                  55                  60

Gly Thr His Val Ser Gly Ile Leu Ser Gly Asn Ala Pro Ser Glu Thr
65              70                  75                  80

Lys Glu Pro Tyr Arg Leu Glu Gly Ala Met Pro Glu Ala Gln Leu Leu
                85                  90                  95

Leu Met Arg Val Glu Ile Val Asn Gly Leu Ala Asp Tyr Ala Arg Asn
            100                 105                 110

Tyr Ala Gln Ala Ile Arg Asp Ala Val Asn Leu Gly Ala Lys Val Ile
            115                 120                 125

Asn Met Ser Phe Gly Asn Ala Ala Leu Ala Tyr Ala Asn Leu Pro Asp
130                 135                 140

Glu Thr Lys Lys Ala Phe Asp Tyr Ala Lys Ser Lys Gly Val Ser Ile
145                 150                 155                 160

Val Thr Ser Ala Gly Asn Asp Ser Ser Phe Gly Gly Lys Thr Arg Leu
                165                 170                 175

Pro Leu Ala Asp His Pro Asp Tyr Gly Val Val Gly Thr Pro Ala Ala
            180                 185                 190

Ala Asp Ser Thr Leu Thr Val Ala Ser Tyr Ser Pro Asp Lys Gln Leu
        195                 200                 205

Thr Glu Thr Ala Met Val Lys Thr Asp Gln Gln Asp Lys Glu Met
    210                 215                 220

Pro Val Leu Ser Thr Asn Arg Phe Glu Pro Asn Lys Ala Tyr Asp Tyr
225                 230                 235                 240

Ala Tyr Ala Asn Arg Gly Met Lys Glu Asp Asp Phe Lys Asp Val Lys
                245                 250                 255
```

```
Gly Lys Ile Ala Leu Ile Glu Arg Gly Asp Ile Asp Phe Lys Asp Lys
            260                 265                 270

Val Ala Asn Ala Lys Lys Ala Gly Ala Val Gly Val Leu Ile Tyr Asp
            275                 280                 285

Asn Gln Asp Lys Gly Phe Pro Ile Glu Leu Pro Asn Val Asp Gln Met
            290                 295                 300

Pro Ala Ala Phe Ile Ser Arg Lys Asp Gly Leu Leu Leu Lys Asp Asn
305                 310                 315                 320

Pro Gln Lys Thr Ile Thr Phe Asn Ala Thr Pro Lys Val Leu Pro Thr
            325                 330                 335

Ala Ser Gly Thr Lys Leu Ser Arg Phe Ser Ser Trp Gly Leu Thr Ala
            340                 345                 350

Asp Gly Asn Ile Lys Pro Asp Ile Ala Ala Pro Gly Gln Asp Ile Leu
            355                 360                 365

Ser Ser Val Ala Asn Asn Lys Tyr Ala Lys Leu Ser Gly Thr Ser
            370                 375                 380

<210> SEQ ID NO 8
<211> LENGTH: 383
<212> TYPE: PRT
<213> ORGANISM: Streptococcus agalactiae

<400> SEQUENCE: 8

Asp Ala Gly Phe Asp Lys Asn His Glu Ala Trp Arg Leu Thr Asp Lys
1               5                   10                  15

Thr Lys Ala Arg Tyr Gln Ser Lys Glu Asp Leu Glu Lys Ala Lys Lys
            20                  25                  30

Glu His Gly Ile Thr Tyr Gly Glu Trp Val Asn Asp Lys Val Ala Tyr
            35                  40                  45

Tyr His Asp Tyr Ser Lys Asp Gly Lys Thr Ala Val Asp Gln Glu His
        50                  55                  60

Gly Thr His Val Ser Gly Ile Leu Ser Gly Asn Ala Pro Ser Glu Thr
65              70                  75                  80

Lys Glu Pro Tyr Arg Leu Glu Gly Ala Met Pro Glu Ala Gln Leu Leu
                85                  90                  95

Leu Met Arg Val Glu Ile Val Asn Gly Leu Ala Asp Tyr Ala Arg Asn
            100                 105                 110

Tyr Ala Gln Ala Ile Arg Asp Ala Ile Asn Leu Gly Ala Lys Val Ile
            115                 120                 125

Asn Met Ser Phe Gly Asn Ala Ala Leu Ala Tyr Ala Asn Leu Pro Asp
130                 135                 140

Glu Thr Lys Lys Ala Phe Asp Tyr Ala Lys Ser Lys Gly Val Ser Ile
145                 150                 155                 160

Val Thr Ser Ala Gly Asn Asp Ser Ser Phe Gly Gly Lys Thr Arg Leu
                165                 170                 175

Pro Leu Ala Asp His Pro Asp Tyr Gly Val Val Gly Thr Pro Ala Ala
            180                 185                 190

Ala Asp Ser Thr Leu Thr Val Ala Ser Tyr Ser Pro Asp Lys Gln Leu
            195                 200                 205

Thr Glu Thr Val Arg Val Lys Thr Ala Asp Gln Gln Asp Lys Glu Met
            210                 215                 220

Pro Val Leu Ser Thr Asn Arg Phe Glu Pro Asn Lys Ala Tyr Asp Tyr
225                 230                 235                 240

Ala Tyr Ala Asn Arg Gly Thr Lys Glu Asp Phe Lys Asp Val Lys
            245                 250                 255
```

```
Gly Lys Ile Ala Leu Ile Glu Arg Gly Asp Ile Asp Phe Lys Asp Lys
            260                 265                 270

Ile Ala Lys Ala Lys Lys Ala Gly Ala Val Gly Val Leu Ile Tyr Asp
        275                 280                 285

Asn Gln Asp Lys Gly Phe Pro Ile Glu Leu Pro Asn Val Asp Gln Met
    290                 295                 300

Pro Ala Ala Phe Ile Ser Arg Lys Asp Gly Leu Leu Leu Lys Asp Asn
305                 310                 315                 320

Pro Gln Lys Thr Ile Thr Phe Asn Ala Thr Pro Lys Val Leu Pro Thr
                325                 330                 335

Ala Ser Gly Thr Lys Leu Ser Arg Phe Ser Ser Trp Gly Leu Thr Ala
            340                 345                 350

Asp Gly Asn Ile Lys Pro Asp Ile Ala Ala Pro Gly Gln Asp Ile Leu
        355                 360                 365

Ser Ser Val Ala Asn Asn Lys Tyr Ala Lys Leu Ser Gly Thr Ser
    370                 375                 380

<210> SEQ ID NO 9
<211> LENGTH: 921
<212> TYPE: PRT
<213> ORGANISM: Streptococcus pyogenes, strain 49

<400> SEQUENCE: 9

Asp Ala Gly Phe Asp Lys Asn His Glu Ala Trp Arg Leu Thr Asp Lys
1               5                   10                  15

Ala Lys Ala Arg Tyr Gln Ser Lys Glu Asp Leu Glu Lys Ala Lys Lys
            20                  25                  30

Glu His Gly Ile Thr Tyr Gly Glu Trp Val Asn Asp Lys Val Ala Tyr
        35                  40                  45

Tyr His Asp Tyr Ser Lys Asp Gly Lys Thr Ala Val Asp Gln Glu His
    50                  55                  60

Gly Thr His Val Ser Gly Ile Leu Ser Gly Asn Ala Pro Ser Glu Thr
65                  70                  75                  80

Lys Glu Pro Tyr Arg Leu Glu Gly Ala Met Pro Glu Ala Gln Leu Leu
                85                  90                  95

Leu Met Arg Val Glu Ile Val Asn Gly Leu Ala Asp Tyr Ala Arg Asn
            100                 105                 110

Tyr Ala Gln Ala Ile Arg Asp Ala Val Asn Leu Gly Ala Lys Val Ile
        115                 120                 125

Asn Met Ser Phe Gly Asn Ala Ala Leu Ala Tyr Ala Asn Leu Pro Asp
130                 135                 140

Glu Thr Lys Lys Pro Phe Val Tyr Ala Lys Ser Lys Gly Val Arg Ile
145                 150                 155                 160

Val Thr Thr Ala Gly Asn Asp Ser Ser Phe Gly Gly Lys Thr Arg Leu
                165                 170                 175

Pro Leu Ala Asp His Pro Asp Tyr Gly Val Val Gly Thr Pro Ala Ala
            180                 185                 190

Ala Asp Ser Thr Leu Thr Val Ala Ser Tyr Ser Pro Asp Asn Gln Leu
        195                 200                 205

Thr Glu Thr Ala Met Val Lys Thr Asp Gln Gln Asp Lys Glu Met
    210                 215                 220

Pro Val Leu Ser Thr Asn Arg Phe Glu Pro Asn Lys Ala Tyr Asp Tyr
225                 230                 235                 240

Ala Tyr Ala Asn Arg Gly Met Lys Glu Asp Phe Lys Asp Val Lys
                245                 250                 255
```

-continued

```
Gly Lys Ile Ala Leu Ile Glu Arg Ser Asp Ile Asp Phe Thr Asp Lys
            260                 265                 270

Ile Ala Asn Ala Lys Lys Ala Gly Ala Val Gly Val Leu Ile Tyr Asp
            275                 280                 285

Asn Gln Asp Lys Gly Phe Pro Ile Glu Leu Pro Asn Val Asp Gln Met
            290                 295                 300

Pro Ala Ala Phe Ile Ser Arg Lys Asp Gly Leu Leu Leu Lys Asp Asn
305                 310                 315                 320

Ser Gln Lys Thr Ile Thr Phe Asn Ala Thr Pro Lys Val Leu Pro Thr
            325                 330                 335

Ala Ser Gly Thr Lys Leu Ser Arg Phe Ser Ser Trp Gly Leu Thr Ala
            340                 345                 350

Asp Gly Asn Ile Lys Pro Asp Ile Ala Ala Pro Gly Gln Asp Ile Leu
            355                 360                 365

Ser Ser Ala Ala Asn Asn Lys Tyr Ala Lys Leu Ser Gly Thr Ser Met
            370                 375                 380

Ser Ala Pro Leu Val Ala Val Ile Met Gly Leu Leu Gln Lys Gln Tyr
385                 390                 395                 400

Glu Thr Gln Tyr Pro Asp Met Thr Gln Ser Glu Arg Leu Asp Leu Ala
            405                 410                 415

Lys Lys Val Leu Met Ser Ser Ala Thr Ala Leu Tyr Asp Glu Asp Glu
            420                 425                 430

Lys Ala Tyr Phe Ser Pro Arg Gln Gln Gly Ala Gly Ala Val Asp Ala
            435                 440                 445

Lys Lys Ala Ser Glu Ala Thr Met Tyr Val Thr Asp Lys Asp Asn Thr
450                 455                 460

Ser Ser Lys Val His Leu Asn Asn Val Ser Asp Lys Phe Glu Val Thr
465                 470                 475                 480

Val Thr Val His Asn Lys Ser Asp Lys Pro His Glu Leu Tyr Tyr Gln
            485                 490                 495

Ala Thr Val Gln Thr Asp Lys Val Asp Gly Lys His Phe Ala Leu Ala
            500                 505                 510

Pro Lys Ala Leu Ile Glu Thr Ser Trp Gln Lys Ile Thr Ile Pro Ala
            515                 520                 525

Asn Ser Ser Lys Gln Val Thr Ile Pro Ile Asp Ile Ser Gln Phe Ser
            530                 535                 540

Lys Asp Leu Leu Ala Gln Met Lys Asn Gly Tyr Phe Leu Glu Gly Phe
545                 550                 555                 560

Val Arg Ile Lys Gln Asp Pro Thr Lys Glu Glu Leu Met Ser Ile Pro
            565                 570                 575

Tyr Ile Gly Phe Arg Gly Asp Phe Gly Asn Leu Ser Ala Leu Glu Lys
            580                 585                 590

Pro Leu Tyr Asp Ser Lys Asp Gly Ser Ser Tyr His Glu Glu Ile
            595                 600                 605

Ser Asp Ala Lys Asp Gln Leu Asp Gly Asp Leu Gln Phe Tyr Ala
            610                 615                 620

Leu Lys Asn Asp Phe Thr Ala Leu Thr Thr Glu Ser Asn Pro Trp Thr
625                 630                 635                 640

Ile Ile Asn Val Val Lys Glu Gly Val Glu Asn Ile Glu Asp Ile Glu
            645                 650                 655

Ser Ser Glu Ile Thr Glu Thr Ile Phe Ala Gly Thr Phe Ala Lys Gln
            660                 665                 670
```

Asp Asp Asp Arg His Tyr Tyr Ile His Arg His Ala Asn Gly Lys Pro
           675                 680                 685

Tyr Ala Ala Ile Ser Pro Asn Gly Asp Gly Asn Arg Asp Tyr Val Gln
    690                 695                 700

Phe His Gly Thr Phe Leu Arg Asn Ala Lys Asn Leu Val Ala Glu Val
705                 710                 715                 720

Leu Asp Lys Glu Gly Asn Val Val Trp Thr Ser Glu Val Thr Glu Gln
                725                 730                 735

Val Val Lys Asn Tyr Asn Asn Asp Leu Ala Ser Thr Leu Gly Ser Thr
            740                 745                 750

Arg Phe Glu Ile Ser Arg Trp Asp Gly Lys Asp Lys Asp Ala Lys Val
            755                 760                 765

Val Ala Asn Gly Thr Tyr Thr Tyr Arg Val Arg Tyr Thr Pro Ile Ser
    770                 775                 780

Ser Gly Ala Lys Glu Gln His Thr Asp Phe Asp Val Ile Val Asp Asn
785                 790                 795                 800

Thr Thr Pro Glu Val Ala Thr Ser Ala Thr Phe Ser Thr Glu Asp Arg
                805                 810                 815

Arg Leu Thr Leu Ala Ser Lys Pro Gln Thr Ser Gln Pro Val Tyr Arg
            820                 825                 830

Glu Arg Ile Ala Tyr Thr Tyr Met Asp Glu Asp Leu Pro Thr Thr Glu
            835                 840                 845

Tyr Ile Ser Pro Asn Glu Asp Gly Thr Phe Thr Leu Pro Glu Glu Ala
    850                 855                 860

Glu Thr Met Glu Gly Ala Thr Val Pro Leu Lys Met Ser Asp Phe Thr
865                 870                 875                 880

Tyr Val Val Glu Asp Met Ala Gly Asn Ile Thr Tyr Thr Pro Val Thr
                885                 890                 895

Lys Leu Leu Glu Gly His Ser Asn Lys Pro Glu Gln Asp Gly Ser Asp
            900                 905                 910

Gln Ala Pro Asp Lys Lys Pro Glu Thr
            915                 920

<210> SEQ ID NO 10
<211> LENGTH: 921
<212> TYPE: PRT
<213> ORGANISM: Streptococcus pyogenes, strain 12

<400> SEQUENCE: 10

Asp Ala Gly Phe Asp Lys Asn His Glu Ala Trp Arg Leu Thr Asp Lys
1               5                   10                  15

Thr Lys Ala Arg Tyr Gln Ser Lys Glu Asp Leu Glu Lys Ala Lys Lys
            20                  25                  30

Glu His Gly Ile Thr Tyr Gly Glu Trp Val Asn Asp Lys Val Ala Tyr
        35                  40                  45

Tyr His Asp Tyr Ser Lys Asp Gly Lys Thr Ala Val Asp Gln Glu His
    50                  55                  60

Gly Thr His Val Ser Gly Ile Leu Ser Gly Asn Ala Pro Ser Glu Thr
65                  70                  75                  80

Lys Glu Pro Tyr Arg Leu Glu Gly Ala Met Pro Glu Ala Gln Leu Leu
                85                  90                  95

Leu Met Arg Val Glu Ile Val Asn Gly Leu Ala Asp Tyr Ala Arg Asn
            100                 105                 110

Tyr Ala Gln Ala Ile Arg Asp Ala Val Asn Leu Gly Ala Lys Val Ile
        115                 120                 125

```
Asn Met Ser Phe Gly Asn Ala Ala Leu Ala Tyr Ala Asn Leu Pro Asp
    130                 135                 140

Glu Thr Lys Lys Ala Phe Asp Tyr Ala Lys Ser Lys Gly Val Ser Ile
145                 150                 155                 160

Val Thr Ser Ala Gly Asn Asp Ser Ser Phe Gly Gly Lys Thr Arg Leu
                165                 170                 175

Pro Leu Ala Asp His Pro Asp Tyr Gly Val Val Gly Thr Pro Ala Ala
                180                 185                 190

Ala Asp Ser Thr Leu Thr Val Ala Ser Tyr Ser Pro Asp Lys Gln Leu
            195                 200                 205

Thr Glu Thr Ala Met Val Lys Thr Asp Asp Gln Gln Asp Lys Glu Met
        210                 215                 220

Pro Val Leu Ser Thr Asn Arg Phe Glu Pro Asn Lys Ala Tyr Asp Tyr
225                 230                 235                 240

Ala Tyr Ala Asn Arg Gly Met Lys Glu Asp Asp Phe Lys Asp Val Lys
                245                 250                 255

Gly Lys Ile Ala Leu Ile Glu Arg Gly Asp Ile Asp Phe Lys Asp Lys
                260                 265                 270

Val Ala Asn Ala Lys Lys Ala Gly Ala Val Gly Val Leu Ile Tyr Asp
            275                 280                 285

Asn Gln Asp Lys Gly Phe Pro Ile Glu Leu Pro Asn Val Asp Gln Met
        290                 295                 300

Pro Ala Ala Phe Ile Ser Arg Lys Asp Gly Leu Leu Leu Lys Asp Asn
305                 310                 315                 320

Pro Gln Lys Thr Ile Thr Phe Asn Ala Thr Pro Lys Val Leu Pro Thr
                325                 330                 335

Ala Ser Gly Thr Lys Leu Ser Arg Phe Ser Ser Trp Gly Leu Thr Ala
            340                 345                 350

Asp Gly Asn Ile Lys Pro Asp Ile Ala Ala Pro Gly Gln Asp Ile Leu
        355                 360                 365

Ser Ser Val Ala Asn Asn Lys Tyr Ala Lys Leu Ser Gly Thr Ser Met
370                 375                 380

Ser Ala Pro Leu Val Ala Gly Ile Met Gly Leu Leu Gln Lys Gln Tyr
385                 390                 395                 400

Glu Thr Gln Tyr Pro Asp Met Thr Pro Ser Glu Arg Leu Asp Leu Ala
                405                 410                 415

Lys Lys Val Leu Met Ser Ser Ala Thr Ala Leu Tyr Asp Glu Asp Glu
                420                 425                 430

Lys Ala Tyr Phe Ser Pro Arg Gln Gln Gly Ala Gly Ala Val Asp Ala
            435                 440                 445

Lys Lys Ala Ser Ala Ala Thr Met Tyr Val Thr Asp Lys Asp Asn Thr
        450                 455                 460

Ser Ser Lys Val His Leu Asn Asn Val Ser Asp Lys Phe Glu Val Thr
465                 470                 475                 480

Val Thr Val His Asn Lys Ser Asp Lys Pro Gln Glu Leu Tyr Tyr Gln
                485                 490                 495

Ala Thr Val Gln Thr Asp Lys Val Asp Gly Lys His Phe Ala Leu Ala
                500                 505                 510

Pro Lys Val Leu Tyr Glu Ala Ser Trp Gln Lys Ile Thr Ile Pro Ala
            515                 520                 525

Asn Ser Ser Lys Gln Val Thr Val Pro Ile Asp Ala Ser Arg Phe Ser
        530                 535                 540
```

```
Lys Asp Leu Leu Ala Gln Met Lys Asn Gly Tyr Phe Leu Glu Gly Phe
545                 550                 555                 560

Val Arg Phe Lys Gln Asp Pro Thr Lys Glu Glu Leu Met Ser Ile Pro
                565                 570                 575

Tyr Ile Gly Phe Arg Gly Asp Phe Gly Asn Leu Ser Ala Val Glu Lys
            580                 585                 590

Pro Ile Tyr Asp Ser Lys Asp Gly Ser Ser Tyr His Glu Ala Asn
        595                 600                 605

Ser Asp Ala Lys Asp Gln Leu Asp Gly Asp Leu Gln Phe Tyr Ala
    610                 615                 620

Leu Lys Asn Asn Phe Thr Ala Leu Thr Thr Glu Ser Asn Pro Trp Thr
625                 630                 635                 640

Ile Ile Lys Ala Val Lys Glu Gly Val Glu Asn Ile Glu Asp Ile Glu
                645                 650                 655

Ser Ser Glu Ile Thr Glu Thr Ile Phe Ala Gly Thr Phe Ala Lys Gln
                660                 665                 670

Asp Asp Asp Ser His Tyr Tyr Ile His Arg His Ala Asn Gly Glu Pro
                675                 680                 685

Tyr Ala Ala Ile Ser Pro Asn Gly Asp Gly Asn Arg Asp Tyr Val Gln
690                 695                 700

Phe Gln Gly Thr Phe Leu Arg Asn Ala Lys Asn Leu Val Ala Glu Val
705                 710                 715                 720

Leu Asp Lys Glu Gly Asn Val Val Trp Thr Ser Glu Val Thr Glu Gln
                725                 730                 735

Val Val Lys Asn Tyr Asn Asn Asp Leu Ala Ser Thr Leu Gly Ser Thr
                740                 745                 750

Arg Phe Glu Lys Thr Arg Trp Asp Gly Lys Asp Lys Asp Gly Lys Val
                755                 760                 765

Val Ala Asn Gly Thr Tyr Thr Tyr Arg Val Arg Tyr Thr Pro Ile Ser
                770                 775                 780

Ser Gly Ala Lys Glu Gln His Thr Asp Phe Asp Val Ile Val Asp Asn
785                 790                 795                 800

Thr Thr Pro Glu Val Ala Thr Ser Ala Thr Phe Ser Thr Glu Asp Arg
                805                 810                 815

Arg Leu Thr Leu Ala Ser Lys Pro Lys Thr Ser Gln Pro Val Tyr Arg
                820                 825                 830

Glu Arg Ile Ala Tyr Thr Tyr Met Asp Glu Asp Leu Pro Thr Thr Glu
                835                 840                 845

Tyr Ile Ser Pro Asn Glu Asp Gly Thr Phe Thr Leu Pro Glu Glu Ala
        850                 855                 860

Glu Thr Met Glu Gly Ala Thr Val Pro Leu Lys Met Ser Asp Phe Thr
865                 870                 875                 880

Tyr Val Val Glu Asp Met Ala Gly Asn Ile Thr Tyr Thr Pro Val Thr
                885                 890                 895

Lys Leu Leu Glu Gly His Ser Asn Lys Pro Glu Gln Asp Gly Ser Gly
                900                 905                 910

Gln Thr Pro Asp Lys Lys Pro Glu Ala
            915                 920

<210> SEQ ID NO 11
<211> LENGTH: 921
<212> TYPE: PRT
<213> ORGANISM: Streptococcus agalactiae
```

-continued

```
<400> SEQUENCE: 11

Asp Ala Gly Phe Asp Lys Asn His Glu Ala Trp Arg Leu Thr Asp Lys
 1               5                  10                  15

Thr Lys Ala Arg Tyr Gln Ser Lys Glu Asp Leu Glu Lys Ala Lys Lys
            20                  25                  30

Glu His Gly Ile Thr Tyr Gly Glu Trp Val Asn Asp Lys Val Ala Tyr
        35                  40                  45

Tyr His Asp Tyr Ser Lys Asp Gly Lys Thr Ala Val Asp Gln Glu His
    50                  55                  60

Gly Thr His Val Ser Gly Ile Leu Ser Gly Asn Ala Pro Ser Glu Thr
 65                  70                  75                  80

Lys Glu Pro Tyr Arg Leu Glu Gly Ala Met Pro Glu Ala Gln Leu Leu
                85                  90                  95

Leu Met Arg Val Glu Ile Val Asn Gly Leu Ala Asp Tyr Ala Arg Asn
            100                 105                 110

Tyr Ala Gln Ala Ile Arg Asp Ala Ile Asn Leu Gly Ala Lys Val Ile
        115                 120                 125

Asn Met Ser Phe Gly Asn Ala Ala Leu Ala Tyr Ala Asn Leu Pro Asp
    130                 135                 140

Glu Thr Lys Lys Ala Phe Asp Tyr Ala Lys Ser Lys Gly Val Ser Ile
145                 150                 155                 160

Val Thr Ser Ala Gly Asn Asp Ser Ser Phe Gly Gly Lys Thr Arg Leu
                165                 170                 175

Pro Leu Ala Asp His Pro Asp Tyr Gly Val Val Gly Thr Pro Ala Ala
            180                 185                 190

Ala Asp Ser Thr Leu Thr Val Ala Ser Tyr Ser Pro Asp Lys Gln Leu
        195                 200                 205

Thr Glu Thr Val Arg Val Lys Thr Ala Asp Gln Gln Asp Lys Glu Met
    210                 215                 220

Pro Val Leu Ser Thr Asn Arg Phe Glu Pro Asn Lys Ala Tyr Asp Tyr
225                 230                 235                 240

Ala Tyr Ala Asn Arg Gly Thr Lys Glu Asp Asp Phe Lys Asp Val Lys
                245                 250                 255

Gly Lys Ile Ala Leu Ile Glu Arg Gly Asp Ile Asp Phe Lys Asp Lys
            260                 265                 270

Ile Ala Lys Ala Lys Lys Ala Gly Ala Val Gly Val Leu Ile Tyr Asp
        275                 280                 285

Asn Gln Asp Lys Gly Phe Pro Ile Glu Leu Pro Asn Val Asp Gln Met
    290                 295                 300

Pro Ala Ala Phe Ile Ser Arg Lys Asp Gly Leu Leu Leu Lys Asp Asn
305                 310                 315                 320

Pro Gln Lys Thr Ile Thr Phe Asn Ala Thr Pro Lys Val Leu Pro Thr
                325                 330                 335

Ala Ser Gly Thr Lys Leu Ser Arg Phe Ser Ser Trp Gly Leu Thr Ala
            340                 345                 350

Asp Gly Asn Ile Lys Pro Asp Ile Ala Ala Pro Gly Gln Asp Ile Leu
        355                 360                 365

Ser Ser Val Ala Asn Asn Lys Tyr Ala Lys Leu Ser Gly Thr Ser Met
    370                 375                 380

Ser Ala Pro Leu Val Ala Gly Ile Met Gly Leu Leu Gln Lys Gln Tyr
385                 390                 395                 400

Glu Thr Gln Tyr Pro Asp Met Thr Pro Ser Glu Arg Leu Asp Leu Ala
                405                 410                 415
```

-continued

```
Lys Lys Val Leu Met Ser Ser Ala Thr Ala Leu Tyr Asp Glu Asp Glu
            420                 425                 430

Lys Ala Tyr Phe Ser Pro Arg Gln Gln Gly Ala Gly Ala Val Asp Ala
            435                 440                 445

Lys Lys Ala Ser Ala Ala Thr Met Tyr Val Thr Asp Lys Asp Asn Thr
            450                 455                 460

Ser Ser Lys Val His Leu Asn Asn Val Ser Asp Lys Phe Glu Val Thr
465                 470                 475                 480

Val Asn Val His Asn Lys Ser Asp Lys Pro Gln Glu Leu Tyr Tyr Gln
                485                 490                 495

Ala Thr Val Gln Thr Asp Lys Val Asp Gly Lys His Phe Ala Leu Ala
            500                 505                 510

Pro Lys Val Leu Tyr Glu Ala Ser Trp Gln Lys Ile Thr Ile Pro Ala
            515                 520                 525

Asn Ser Ser Lys Gln Val Thr Val Pro Ile Asp Ala Ser Arg Phe Ser
            530                 535                 540

Lys Asp Leu Leu Ala Gln Met Lys Asn Gly Tyr Phe Leu Glu Gly Phe
545                 550                 555                 560

Val Arg Phe Lys Gln Asp Pro Lys Lys Glu Glu Leu Met Ser Ile Pro
                565                 570                 575

Tyr Ile Gly Phe Arg Gly Asp Phe Gly Asn Leu Ser Ala Leu Glu Lys
            580                 585                 590

Pro Ile Tyr Asp Ser Lys Asp Gly Ser Ser Tyr His Glu Ala Asn
            595                 600                 605

Ser Asp Ala Lys Asp Gln Leu Asp Gly Asp Gly Leu Gln Phe Tyr Ala
            610                 615                 620

Leu Lys Asn Asn Phe Thr Ala Leu Thr Thr Glu Ser Asn Pro Trp Thr
625                 630                 635                 640

Ile Ile Lys Ala Val Lys Glu Gly Val Glu Asn Ile Glu Asp Ile Glu
                645                 650                 655

Ser Ser Glu Ile Thr Glu Thr Ile Leu Ala Gly Thr Phe Ala Lys Gln
            660                 665                 670

Asp Asp Asp Ser His Tyr Tyr Ile His Arg His Ala Asn Gly Lys Pro
            675                 680                 685

Tyr Ala Ala Ile Ser Pro Asn Gly Asp Gly Asn Arg Asp Tyr Val Gln
            690                 695                 700

Phe Gln Gly Thr Phe Leu Arg Asn Ala Lys Asn Leu Val Ala Glu Val
705                 710                 715                 720

Leu Asp Lys Glu Gly Asn Val Val Trp Thr Ser Glu Val Thr Glu Gln
                725                 730                 735

Val Val Lys Asn Tyr Asn Asn Asp Leu Ala Ser Thr Leu Gly Ser Thr
            740                 745                 750

Arg Phe Glu Lys Thr Arg Trp Asp Gly Lys Asp Lys Asp Gly Lys Val
            755                 760                 765

Val Ala Asn Gly Thr Tyr Thr Tyr Arg Val Arg Tyr Thr Pro Ile Ser
            770                 775                 780

Ser Gly Ala Lys Glu Gln His Thr Asp Phe Asp Val Ile Val Asp Asn
785                 790                 795                 800

Thr Thr Pro Glu Val Ala Thr Ser Ala Thr Phe Ser Thr Glu Asp Arg
                805                 810                 815

Arg Leu Thr Leu Ala Ser Lys Pro Lys Thr Ser Gln Pro Val Tyr Arg
            820                 825                 830
```

-continued

```
Glu Arg Ile Ala Tyr Thr Tyr Met Asp Glu Asp Leu Pro Thr Thr Glu
        835                 840                 845

Tyr Ile Ser Pro Asn Glu Asp Gly Thr Phe Thr Leu Pro Glu Glu Ala
    850                 855                 860

Glu Thr Thr Glu Gly Ala Thr Val Pro Leu Lys Met Ser Asp Phe Thr
865                 870                 875                 880

Tyr Val Val Glu Asp Met Ala Gly Asn Ile Thr Tyr Thr Pro Val Thr
                885                 890                 895

Lys Leu Leu Glu Gly His Ser Asn Lys Pro Glu Gln Asp Gly Ser Asp
            900                 905                 910

Gln Ala Pro Asp Lys Lys Pro Glu Ala
        915                 920
```

STREPTOCOCCAL C5A PEPTIDASE VACCINE

This application is a divisional of U.S. patent application Ser. No. 08/589,756 filed on Jan. 22, 1996, now U.S. Pat. No. 5,846,547.

The invention was made with the support of NIH Grant No. AI 20016-11. The U.S. government has certain rights in the invention.

BACKGROUND OF THE INVENTION

There are several different β-hemolytic streptococcal species that have been identified. *Streptococcus pyogenes*, also called group A streptococci, is a common bacterial pathogen of humans. Primarily a disease of children, it causes a variety of infections including pharyngitis, impetigo and sepsis in humans. Subsequent to infection, autoimmune complications such as rheumatic fever and acute glomerulonephritis can occur in humans. This pathogen also causes severe acute diseases such as scarlet fever, necrotizing fasciitis and toxic shock.

Sore throat caused by group A streptococci, commonly called "strep throat," accounts for at least 16% of all office calls in a general medical practice, depending on the season. Hope-Simpson, E., "*Streptococcus pyogenes* in the throat: A study in a small population, 1962–1975," *J. Hyg. Camb.*, 87:109–129 (1981). This species is also the cause of the recent resurgence in North America and four other continents of toxic shock associated with necrotizing fasciitis. Stevens, D. L., "Invasive group A streptococcus infections," *Clin. Infect. Dis.*, 14:2–13 (1992). Also implicated in causing strep throat and occasionally in causing toxic shock are groups C and G streptococci. Hope-Simpson, E., "Streptococcus pyogenes in the throat: A study in a small population, 1962–1975," *J. Hyg. Camb.*, 87:109–129 (1981).

Group B streptococci, also known as *Streptococcus agalactiae*, are responsible for neonatal sepsis and meningitis. T. R. Martin et al., "The effect of type-specific polysaccharide capsule on the clearance of group B streptococci from the lung of infant and adult rats", *J. Infect Dis.*, 165:306–314 (1992). Although frequently a member of vaginal mucosal flora of adult females, from 0.1 to $0.5/1000$ newborns develop serious disease following infection during delivery. In spite of the high mortality from group B streptococcal infections, mechanisms of the pathogenicity are poorly understood. Martin, T. R., et al., "The effect of type-specific polysaccharide capsule on the clearance of Group B streptococci from the lung of infant and adult rats," *J. Infect. Dis.*, 165:306–314 (1992).

Streptococcal infections are currently treated by antibiotic therapy. However, 25–30% of those treated have recurrent disease and/or shed the organism in mucosal secretions. At present no means is available to prevent streptococcal infections. Historically, streptococcal vaccine development has focused on the bacterium's cell surface M protein. Bessen, D., et al., "Influence of intranasal immunization with synthetic peptides corresponding to conserved epitopes of M protein on mucosal colonization by group A streptococci," *Infect. Immun.*, 56:2666–2672 (1988); Bronze, M. S., et al., "Protective immunity evoked by locally administered group A streptococcal vaccines in mice," *Journal of Immunology*, 141:2767–2770 (1988).

Two major problems will limit the use, marketing, and possibly FDA approval, of a M protein vaccine. First, more than 80 different M serotypes of *S. pyogenes* exist and new serotypes continually arise. Fischetti, V. A., "Streptococcal M protein: molecular design and biological behavior, *Clin. Microbiol. Rev.*, 2:285–314 (1989). Thus, inoculation with one serotype-specific M protein will not likely be effective in protecting against other M serotypes. The second problem relates to the safety of an M protein vaccine. Several regions of the M protein contain antigenic epitopes which are immunologically cross-reactive with human tissue, particularly heart tissue. The N-termini of M proteins are highly variable in sequence and antigenic specificity. Inclusion of more than 80 different peptides, representing this variable sequence, in a vaccine would be required to achieve broad protection against group A streptococcal infection. New variant M proteins would still continue to arise, requiring ongoing surveillance of streptococcal disease and changes in the vaccine composition. In contrast, the carboxyl-termini of M proteins are conserved in sequence. This region of the M protein, however, contains an amino acid sequence which is immunologically cross-reactive with human heart tissue. This property of M protein is thought to account for heart valve damage associated with rheumatic fever. P. Fenderson et al., "Tropomyosinsharies immunologic epitopes with group A streptococcal M proteins, *J. Immunol.* 142:2475–2481 (1989). In an early trial, children who were vaccinated with M protein in 1979 had a ten fold higher incidence of rheumatic fever and associated heart valve damage. Massell, B. F., et al., "Rheumatic fever following streptococcal vaccination, *JAMA*, 207:1115–1119 (1969).

Other proteins under consideration for vaccine development are the erythrogenic toxins, streptococcal pyrogenic exotoxin A and streptococcal pyrogenic exotoxin B. Lee, P. K., et al., "Quantification and toxicity of group A streptococcal pyrogenic exotoxins in an animal model of toxic shock syndrome-like illness," *J. Clin. Microb.*, 27:1890–1892 (1989). Immunity to these proteins could prevent the deadly symptoms of toxic shock, but will not prevent colonization by streptococci, nor likely lower the incidence of strep throat. Estimates suggest that the incidence of toxic shock infections is 10 to 20 cases per 100,000 population; therefore, use of these proteins to immunize the general population against toxic shock is neither practical nor economically feasible.

Thus, there remains a continuing need for an effective means to prevent or ameliorate streptococcal infections. More specifically, a need exists to develop compositions useful in vaccines to prevent or ameliorate colonization of host tissues by streptococci, thereby reducing the incidence of strep throat and impetigo. Elimination of sequelae such as rheumatic fever, acute glomerulonephritis, sepsis, toxic shock and necrotizing fasciitis would be a direct consequence of reducing the incidence of acute infection and carriage of the organism. A need also exists to develop compositions useful in vaccines to prevent or ameliorate infections caused by all β-hemolytic streptococcal species, namely groups A, B, C and G.

SUMMARY OF THE INVENTION

The present invention provides a vaccine, and methods of vaccination, effective to prevent or reduce the incidence of β-hemolytic Streptococcus in susceptible mammals, including humans, and domestic animals such as dogs, cows, pigs and horses. The vaccine contains an immunogenic amount of streptococcal C5a peptidase (SCP), or one or more immunogenic fragments or mutants thereof in combination with a physiologically-acceptable, non-toxic vehicle. The vaccine may comprise a fragment or mutant SCP that lacks SCP enzymatic activity (dSCP). It may also contain an immunological adjuvant. The vaccine can be used to prevent colonization of group A Streptococcus, group B Streptococcus, group C Streptococcus or group G Streptococcus. The vaccine may comprise an immunogenic recombinant streptococcal C5a peptidase conjugated or linked to an immunogenic peptide or to an immunogenic polysaccharide.

The streptococcal C5a peptidase vaccine can be administered by subcutaneous or intramuscular injection. Alternatively, the vaccine can be administered by oral ingestion or intranasal inoculation.

As described in the working examples below, an SCP gene (scpA49) was cloned into an *E. coli* expression vector (pGex-4T-1). The transferase-SCP fusion from the *E. coli* clone was expressed and purified. The purified recombinant SCP (dSCP) was then used to immunize mice. The vaccinated mice and a control group of mice were then challenged with wild-type Streptococci. The mice receiving the recombinant SCP vaccine were free of streptococci soon after infection, whereas 30–50% of the control group were culture positive for many days. Therefore, the recombinant SCP was effective as a vaccine against β-hemolytic Streptococci.

BRIEF DESCRIPTION OF THE DRAWINGS

FIG. 2. Alignment of the amino acid sequence of SCP from group A SEQ ID NO:6 corresponds to the region consisting of amino acid residues 130 through 512 of SEQ ID NO:1. SEQ ID NO:7 corresponds to the region consisting of amino acid residues 130 through 512 of SEQ ID NO:2. SEQ ID NO:8 corresponds to the region consisting of amino acid residues 130 through 512 of SEQ ID NO:3. SEQ ID NO:9 corresponds to amino acid residues 130 through 1050 of SEQ ID NO:1. SEQ ID NO:10 corresponds to amino acid residues 130 through 1050 of SEQ ID NO:2. SEQ ID NO:11 corresponds to amino acid residues 130 through 1050 of SEQ ID NO:3. streptococci strain 49, group A streptococci strain 12 and group B streptococci (SEQ ID NO:1, SEQ ID NO:2, and SEQ ID NO:3, respectively). The sequences are identical except for the indicated amino acid positions. The triangle (Δ) indicates the predicted cleavage point of the signal peptidase. Amino acids predicted to be in the enzyme's active site are marked by asterisks. Deletions in the amino acid sequence are indicated by dots and are boxed.

DETAILED DESCRIPTION OF THE INVENTION

An important first line of defense against infection by many bacterial pathogens is the accumulation of phagocytic polymorphonuclear leukocytes (PMNs) and mononuclear cells at the site of infection. Attraction of these cells is mediated by chemotactic stimuli, such as host factors or factors secreted by the invading organism. The C5a chemoattractant is pivotal to the stimulation of this inflammatory response in mammals. C5a is a 74 residue glycopeptide cleaved from the fifth component (C5) of complement. Phagocytic cells respond in a directed manner to a gradient of C5a and accumulate at the site of infection. C5a may be the most immediate attractant of phagocytes during inflammation. As PMNs infiltrate an inflammatory lesion they secrete other chemokines, such as IL8, which further intensify the inflammatory response.

Streptococcal C5a peptidase (SCP) is a proteolytic enzyme located on the surface of pathogenic streptococci where it destroys C5a, as C5a is locally produced. SCP specifically cleaves the C5a chemotaxin at the PMN binding site (between $His^{67}$-$Lys^{68}$ residues of C5a) and removes the seven most C-terminal residues of C5a. This cleavage of the PMN binding site eliminates the chemotactic signal. Cleary, P., et al., "Streptococcal C5a peptidase is a highly specific endopeptidase," *Infect. Immun.*, 60:5219–5223 (1992); Wexler, D. E., et al., "Mechanism of action of the group A streptococcal C5a inactivator," *Proc. Natl. Acad. Sci. USA*, 82:8144–8148 (1985).

Figure 1:
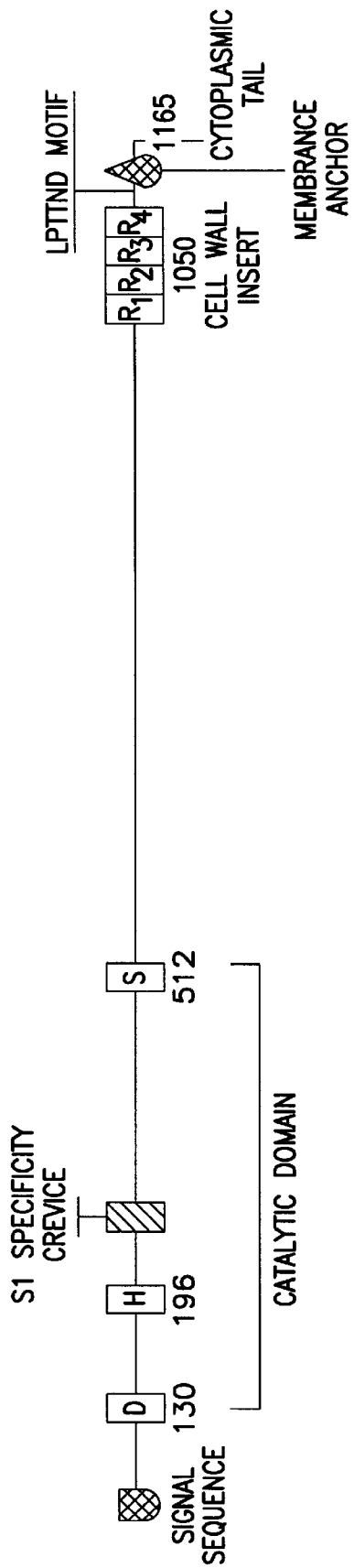
FIG. 1. Architecture of C5a peptidase from β-hemolytic streptococci. D indicates an aspartic acid residue; H indicates histidine; S indicates serine; L indicates leucine; P indicates proline; T indicates threonine; and N indicates asparagine. $R_1$, $R_2$, $R_3$ and $R_4$ indicate repeated sequences. The numbers indicate the amino acid residue position in the peptidase.

SCP from group A streptococci is a subtilisin-like serine protease with an $M_r$ of 124,814 da and with a cell wall anchor motif which is common to many gram⁺ bacterial surface proteins. The architecture of C5a peptidase is given in FIG. 1. The complete nucleotide sequence of the streptococcal C5a peptidase gene of *Streptococcus pyogenes* has been published. Chen, C., and Cleary, P., "Complete nucleotide sequence of the streptococcal C5a peptidase gene of *Streptococcus pyogenes*," *J. Biol. Chem.*, 265:3161–3167 (1990). In contrast to Subtilisins, SCP has a very narrow substrate specificity. This narrow specificity is surprising in light of the marked similarities between their catalytic domains. Cleary, P., et al., "Streptococcal C5a peptidase is a highly specific endopeptidase," *Infect. Immun.*, 60:5219–5223 (1992). Residues involved in charge transfer are conserved, as are residues on both sides of the binding pocket, however, the remaining amino acid sequence of SCP is unrelated to that of Subtilisins. More than 40 serotypes of Group A streptococci were found to produce SCP protein or to harbor the gene. Cleary, P., et al., "A streptococcal inactivator of chemotaxis: a new virulence factor specific to group A streptococci," in *Recent Advances in Streptococci and Streptococcal Disease* p.179–180 (S. Kotami and Y. Shiokawa ed.; Reedbooks Ltd., Berkshire, England; 1984); Podbielski, A., et al., "The group A streptococcal virR49 gene controls expression of four structural vir regulon genes," *Infect. Immun.*, 63:9–20 (1995).

A C5a peptidase enzyme associated with group B streptococci has also been identified. Hill, H. R, et al., "Group B streptococci inhibit the chemotactic activity of the fifth component of complement," *J. Immunol.* 141:3551–3556 (1988). Restriction mapping and completion of the scpB nucleotide sequence showed that scpb is 97–98% similar to scpA. See FIG. 2 for comparison of the amino acid sequence of SCP from group A streptococci strain 49, group A streptococci strain 12 and group B streptococci (SEQ ID NO:1, SEQ ID NO:2, and SEQ ID NO:3, respectively). More than 30 strains, representing all serotypes of group B streptococci carry the scpB gene. Cleary P. P., et al. "Similarity between the Group B and A streptococcal C5a Peptidase genes," *Infect. Immun.* 60:4239–4244 (1992); Suvorov A. N., et al., "C5a peptidase gene from group B streptococci," in *Genetics and Molecular Biology of Streptococci, Lactococci, and Enterococci* p. 230–232 (G. Dunny, P. Cleary and L McKay (ed.); American Society for Microbiology, Washington, D.C.; 1991).

Human isolates of groups G and C streptococci also harbor scpA-like genes. Some group G strains were shown to express C5a specific protease activity on their surface. Cleary, P. P., et al., "Virulent human strains of group G streptococci express a C5a peptidase enzyme similar to that produced by group A streptococci," *Infect. Immun.*, 59:2305–2310 (1991). Therefore, all serotypes (>80) of group A streptococci, group B streptococci, group C streptococci and group G streptococci produce the SCP enzyme.

SCP assists streptococci to colonize a potential infection site, such as the nasopharyngeal mucosa, by inhibiting the influx of phagocytic white cells to the site of infection. This impedes the initial clearance of the streptococci by the host. The impact of SCP on inflammation, C5a leukocyte-chemotaxis and streptococcal virulence was examined using streptococcal strains with well-defined mutations in the protease structural gene. SCP mutants were constructed by targeted plasmid insertion and by replacement of the wild type gene with scpA containing a specific internal deletion. Mutants lacked C5a protease activity and did not inhibit the chemotactic response of human or mouse PMNs to C5a in vitro.

A mouse connective tissue air sac model was used to confirm that SCP retards the influx of phagocytic cells and clearance of streptococci from the site of infection. A connective tissue air sac is generated by injecting a small amount of air and PBS (with or without streptococcus in it) with a 25-gauge needle under the skin on the back of a mouse. Boyle, M. D. P. et al., "Measurement of leukocyte chemotaxis in vivo," *Meth. Enzymol.*, 162:101:115 (1988). At the end of the experiment, the mice were euthanized by cervical dislocation, the air sacs dissected from the animals, and the air sacs homogenized in buffer. An advantage of the air sac model is that the air sac remains inflated for several days and free of inflammation, unless an irritant is injected. Thus, injected bacteria and the resulting inflammatory response remains localized over short periods of infection.

The air sac model was modified to compare clearance of wild type SCP+ and SCP− streptococci, (i.e., group A streptococci which carried a mutant non-functional form of SCP) and to analyze the cellular infiltrate at an early stage of infection. Tissue suspensions were assayed for viable streptococci on blood agar plates and the cellular infiltrate was analyzed by fluorescent cell sorting (FACS). In FACS analysis, individual cells in suspension are labelled with specific fluorescent monoantibodies. Aliquots of labelled cells are injected into a FAC-Scan flowcytometer, or fluorescent cell sorter, which counts cells based on their unique fluorescence. The experiments using the air sac model indicated that streptococci that were SCP+ were more virulent than streptococci that were SCP−.

A study was performed to measure production of human antibody, both IgG and IgA, against SCP in human sera and saliva. O'Connor, SP, et al., "The Human Antibody Response to Streptococcal C5a Peptidase," *J. Infect. Dis.* 163:109-16 (1991). Generally, sera and saliva from young, uninfected children lacked antibody to SCP. In contrast, most sera and saliva specimens from healthy adults had measurable levels of anti-SCP IgG and SCP-specific secretory IgA (anti-SCP sigA). Paired acute and convalescent sera from patients with streptococcal pharyngitis possessed significantly higher levels of anti-SCP IgG than did sera from healthy individuals. Sera containing high concentrations of anti-SCP immunoglobulin were capable of neutralizing SCP activity. Detection of this antibody in >90% of the saliva specimens obtained from children who had recently experienced streptococcal pharyngitis demonstrated that children can produce an antibody response.

Even though the human subjects produced IgG and IgA against SCP in response to a natural streptococcal infection, it was not known whether the anti-SCP immunoglobulin provides any protection against infection. The basis for immunity to streptococcal infection following natural infection is poorly understood. Further, it was not known if the SCP protein could act as a vaccine against β-hemolytic streptococcal colonization or infection. First, a study was performed to examine the role of SCP in colonization of the nasopharynx. Following intranasal infection with live group A streptococci, throat cultures were taken daily for up to ten days. Wild type and isogenic SCP-deficient mutant streptococci were compared for the ability to persist in the throat over this ten day period. As predicted, the SCP-deficient mutant streptococci were cleared from the nasopharynx more rapidly.

The same intranasal mouse model was used to test the capacity of SCP to induce immunity which will prevent colonization. A mutant form of the recombinant scpA49 gene (lacking 848–1033 nucleotides from the 5' end and 3941–4346 nucleotides from the 3' end of the gene) was cloned into and expressed from the high expression vector pGEX-4T-1. Enzymatically defective SCP protein (dSCP) was purified from an *E. coli* recombinant by affinity chromatography. Sera from rabbits vaccinated intradermally with this protein preparation neutralized SCP activity in vitro. Purified protein (40 µg) was administered intranasally to mice over a period of five weeks. Immunized mice cleared streptococci in 1–2 days; whereas, throat cultures of non-immunized mice remained positive for up to 10 days. The experiment was repeated on three sets of mice, vaccinated with three separate preparations of a SCP protein.

The present invention thus provides a vaccine for use to protect mammals against β-hemolytic Streptococcus colonization or infection. In one embodiment of this invention, as is customary for vaccines, the streptococcal C5a peptidase, variant or fragment thereof, can be delivered to a mammal in a pharmacologically acceptable vehicle. As one skilled in the art will appreciate, it is not necessary to use the entire protein. A selected portion of the polypeptide (for example, a synthetic immunogenic polypeptide corresponding to a portion of the streptococcal C5a peptidase) can be used.

As one skilled in the art will also appreciate, it is not necessary to use a polypeptide that is identical to the native SCP amino acid sequence. The amino acid sequence of the immunogenic polypeptide can correspond essentially to the native SCP amino acid sequence. As used herein "correspond essentially to" refers to a polypeptide sequence that will elicit a protective immunological response at least substantially equivalent to the response generated by native SCP. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response.

Alternatively, the SCP can be conjugated or linked to another peptide or to a polysaccharide. For example, immunogenic proteins well-known in the art, also known as "carriers," may be employed. Useful immunogenic proteins include keyhole limpet hemocyanin (KLH), bovine serum albumin (BSA), ovalbumin, human serum albumin, human gamma globulin, chicken immunoglobulin G and bovine gamma globulin. Useful immunogenic polysaccharides include group A Streptococci polysaccharide, C-polysaccharide from group B Streptococci, or the capsular polysaccharide of *Streptococci pnuemoniae*. Alternatively, polysaccharides of other pathogens that are used as vaccines can be conjugated or linked to SCP.

To immunize a subject, the SCP or an immunologically active fragment or mutant thereof, is administered parenterally, usually by intramuscular or subcutaneous injection in an appropriate vehicle. Other modes of administration, however, such as oral delivery or intranasal delivery, are also acceptable. Vaccine formulations will contain an effective amount of the active ingredient in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the SCP or fragment thereof in one or more doses. Multiple doses may be administered as is required to maintain a state of immunity to streptococci.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the purified SCP, subunit or mutant thereof, can be isolated, lyophilized and stabilized. The SCP peptide may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.*, 30:3–15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

The application of SCP, subunit or mutant thereof, for vaccination of a mammal against colonization offers advantages over other vaccine candidates. Prevention of colonization or infection by inoculation with a single protein will not only reduce the incidence of the very common problems of strep throat and impetigo, but will also eliminate sequelae such as rheumatic fever, acute glomerulonephritis, sepsis, toxic shock and necrotizing fascitis.

The following examples are intended to illustrate but not limit the invention.

EXAMPLE 1

Construction of Insertion and Deletion Mutants in scpA49 and scpA6 a) Bacterial strains and culture conditions. *S. pyogenes* strain CS101 is a serotype M49, and OF$^+$ strain. CS159 is a clinical isolate with a deletion which extends through the M gene cluster and scpA. A spontaneous, streptomycin resistant derivative of strain CS101, named CS101Sm, was selected by plating streptococci from a stationary phase culture on tryptose blood agar containing streptomycin (200 µg/ml). CS101::pG$^+$host5 is strain CS101 with pG$^+$host5 integrated into the chromosome at an unknown location, but outside scpA and the emm gene cluster. *Escherichia coli* strain ER1821 (from New England Biolabs, Inc. Beverly, Mass.) was used as the recipient for the suicide vector, plasmid pG$^+$host5. Plasmid pG$^+$host5 was obtained from Appligene, Inc. Pleasanton, Calif. Streptococci were grown in Todd-Hewitt broth supplemented with 2% neopeptone or 1% yeast extract, or on tryptose agar plates with 5% sheep blood. *E. coli* strain ER1821 containing plasmid pG$^+$host5 was grown in LB broth with erythromycin (300 µg/ml). Streptococci with plasmid pG$^+$host5 were cultured in Todd-Hewitt broth with 1% yeast extract (THY) containing 1 µg/ml of erythromycin (Erm).

Figure 3:
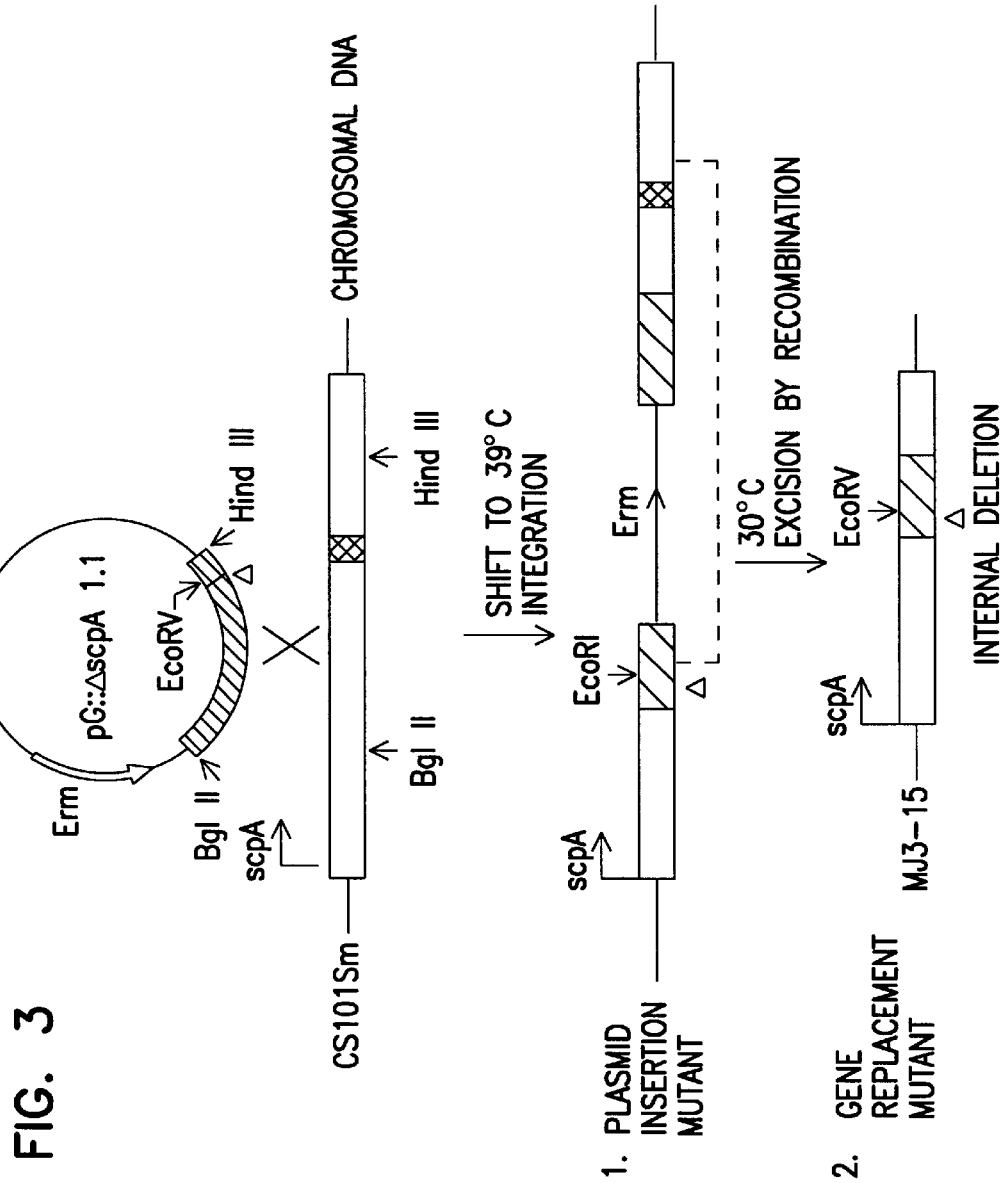
FIG. 3. Construction of SCP insertion and deletion mutants. Black box indicates deleted region.

SCP refers to streptococcal C5a peptidase from β-hemolytic Streptococcus generally. SCPA12, SCPA49, SCPA6 are the specific peptidases from group A Streptococcus M type 12, 49 and 6 strains, respectively. The term scpA refers to the gene encoding SCP from group A streptococci. ScpA12, scpA6 and scpA49 are the genes encoding the SCPA12, SCPA49 and SCPA6 peptidases. SCPB and scpB refer to the peptidase and gene from group B streptococci. The amino acid sequences for SCPA49 (SEQ ID NO:1), SCPA12 (SEQ ID NO:2) and SCPB (SEQ ID NO:3) are given in FIG. 2.

b) Construction of scpA insertion mutant. Well-defined insertion mutants of scpA were constructed using plasmid insertion and gene replacement methods. An internal scpA49 BglII-BamHI fragment, the insertion target, was ligated into the thermosensitive shuttle vector pG$^+$host5 to form plasmid pG::scpA1.2 and transformed into *E. coli* ER1821 (FIG. 3). The pG$^+$host5 vector contains an *E. coli* origin of replication that is active at 39° C., a temperature sensitive Gram$^+$ origin of replication (active at 30° C. and inactive at 39° C. in streptococci), and an erythromycin resistance gene for selection. High temperature forces the plasmid to integrate into the chromosomal DNA of group A streptococci by homologous recombinant at frequencies ranging from $10^{-2}$ to $10^{-3}$.

Recombinant plasmid DNA pG::scpA1.2 was electroporated into CS101 recipient cells. Transformants were selected on THY-agar plates containing 1 μg/ml erythromycin at 30° C. Chromosomal integrants which resulted from recombination between the plasmid insert and the chromosomal scpA were selected by erythromycin resistance at 39° C. Two insertion mutants, M14 and M16, were analyzed. EmrS revertants of strain M14 and M16 were obtained by passage in THY without antibiotic at 30° C. and finally plated at 37° C. without Erm selection. Colonies that had lost the plasmid were isolated to confirm that the mutant phenotype resulted from insertion of the plasmid into scpA49, rather than from a simultaneous unrelated mutation.

c) Introduction of a defined deletion into scpA. A mutant strain with a defined deletion internal to scpA was constructed to eliminate the possibility that insertions in scpA could be polar and reduce expression of downstream genes, unknown genes which could also contribute to the organism's virulence. First, a defined deletion in BglII-HindIII fragment of scpA was produced by inside-out PCR with primer 1 (5'-GGGGGGGAATTC GTAGCGGGTATCATGGGAC- 3'), SEQ ID NO:4, and primer 2 (5'-GGGGGGGAATTC GGGTGCTGCAATATCTGGC- 3'), SEQ ID NO:5. Underlined nucleotides correspond to scpA sequences with coordinates 2398 and 2322, respectively, and the bold faced nucleotides correspond to a EcoRI recognition site. The primers were selected to produce an in-frame deletion in the scpA gene. These primers copy plasmid DNA in opposite directions and define the boundaries of the deletion. Innis, M. A., et al., eds., PCR Protocols A Guide to Methods and Applications (Academic Press, 1990). Plasmid pG::scpA1.2 DNA was used as template.

The amplified product was digested with EcoRI and ligated to plasmid pG+host5. The resulting plasmid pG::ΔscpA1.1 contained an 76 bp deletion internal to scpA. This in-frame deletion removed 25 amino acids, including the serine which forms part of the predicted catalytic center of serine proteases. Chen, C., and Cleary, P., "Complete nucleotide sequence of the streptococcal C5a peptidase gene of Streptococcus pyogenes," J. Biol. Chem., 265:3161–3167 (1990). An EcoRV site was created at the point of deletion. DNA which overlaps the deletion was sequenced to confirm the boundaries of the deletion.

The plasmid pG::scpA1.1, which contains the deletion, was transformed into E. coli ER1821. Colonies were selected for ErmR and then screened for the appropriate scpA deletion using miniprep plasmid DNA restricted by EcoRI. The precise boundaries of the deletion were confirmed by DNA sequencing. Plasmid pG::ΔscpA1.1 was electroporated into strain CS101Sm as described above, then integrants were selected by grown on Erm at 39° C. Integration of the plasmid into the chromosome of the M49 strain CS101sm using high temperature selection. The insertion location was confirmed by PCR. Growth of CS101Sm (pG::scpA1.1) at low temperature without erythromycin selection resulted in high frequency segregation of ErmS revertants which have lost the plasmid by random deletion event or by excision due to recombination between the duplicated scpA sequences created by the insertion. Two deletion mutants were identified, MJ2-5 and MJ3-15, and were studied further. The chromosomal deletion left behind by recombinational excision of plasmid pG::scpA1.1 was defined by PCR and Southern hybridization to EcoRV digested DNA.

d) In vitro effects on SCP. The impact of insertions and deletions on the expression of SCP antigen and peptidase activity was assessed by Western blot and PMNs adherence assays. Streptococci were incubated in 100 ml THY at 37° C. overnight. The culture pellet was washed two times in 5 ml cold 0.2 M NaAcetate (pH 5.2), then suspended in 1 ml TE-sucrose buffer (20% sucrose 10 mM Tris, 1 mM EDTA, pH 7.0) and 40 μl Mutanolysin. The mixture was rotated at 37° C. for 2 hr, then centrifuged 5 min at 4500 rpm. Supernatants contained protease inhibitor, 100 mM phenylmethyl sulfonyl fluoride (PMSF). Electrophoresis and Western blotting methods were performed as described in Laemmli, U. K., "Cleavage of structural proteins during the assembly of the head of bacteriophage T4," Nature 227:680–685 (1970). For colony blots, colonies were grown on THY-agar plates, printed onto nitrocellulose membrane (BioBlot-Nc, Costor, Cambridge, Mass.), fixed under an infrared lamp for 10 min. and exposed to antibody. O'Connor, S. P. and Cleary, P. P., "In vivo Streptococcus pyogenes C5a peptidase activity," J. Infect. Dis. 156:495–506 (1987). The primary antiserum used to detect SCP protein on Western and colony blots was prepared by immunization of a rabbit with purified recombinant SCP protein. Binding was detected by anti-rabbit antibody alkaline phosphatase conjugate.

C5a peptidase activity was measured using a PMN adherence assay. Booth, S. A. et al., "Dapsone suppresses integrin-mediated neutrophil adherence finction," J. Invest. Dermatol. 98:135–140 (1992). After incubation of C5a (Sigma, St. Louis, Mo.) with streptococcal extracts or purified protease, residual C5a can activate PMNs to become adherent to BSA coated wells. First, microtiter wells were coated with 0.5% BSA in PBS and incubated for 1 hr at 37° C. Human PMNs were isolated by centrifugation in Ficoll Hypaque (Sigma, St. Louis, Mo.). 40 μl of intact streptococci or protein extracts were incubated with 20 μl of 5 μM C5a in 340 μl of PBS with 1% glucose and 0.1% $CaCl_2$ at 37° C. for 45 min. BSA-coated wells were washed with PBS, and resuspended PMNs and residual C5a were added to wells. The mixture was incubated for 45 min at 37° C. in 7% $CO_2$. Finally, wells were washed to remove nonadherent PMNs. Adherent PMNs were stained with crystal violet and the $OD_{570nm}$ was read in an ELISA reader. The optical density is proportional to the amount of residual C5a or inversely proportional to the amount of SCP activity.

Insertion mutants completely lacked SCPA49 antigen; whereas, deletion mutants MJ2-5 and MJ3-15, as expected produced SCP antigen. Both whole cells and mutanolysin protein extracts from M14, M16, M2-5 and MJ3-15 lacked the ability to destroy rC5a activated adherence of PMNs to microtiter plates. A small amount of residual inhibitory activity (10–15%) associated with mutant extracts may be due to toxic effects of the extract on the neutrophils.

EXAMPLE 2

SCP Delays Recruitment of Phagocytes and Clearance of Streptococci from Subdermal Sites of Infection In order to verify that SCP was responsible for the inactivation of C5a, the insertion and deletion mutants of scpA were constructed as described in Example 1 above, and tested for activity. When insertions or deletions were introduced into scpA, the mutant SCP was not able to destroy C5a-activated adherence of PMNs to microtiter plates.

The impact of mutations in scpA on virulence was tested using an animal model where streptococci remained localized, and where the influx of inflammatory cells could be analyzed. To test the hypothesis that SCP functions very early to retard initial clearance of the organism, the fate of SCP⁺ and SCP⁻ streptococci just 4 hours after inoculation of connective tissue air sacs was compared. Moreover, the dissemination of streptococci to lymph nodes and spleens after this short period of infection was also assessed. CD1 male outbred mice (25 g) obtained from Charles River Breeding Laboratory, Wilmington, Mass. were used for all experiments. A connective tissue air sac was generated by injecting 0.9 ml of air and 0.1 ml group A streptococci diluted in PBS with a 25-gauge needle under the skin on the back of the mouse. In some experiments the SCP⁺ CS101::pG⁺host5 was used as a positive control. In other experiments strain CS101Sm was used as the positive control. Mice were euthanized by cervical dislocation 4 hours after infection. Where indicated all four inguinal lymph nodes, spleen and air sac were dissected from the animals and homogenized in PBS. Tissue suspensions were assayed for viable colony forming unit (CFU) on blood agar plates containing 1 $\mu$g/ml erythromycin or 200 $\mu$g/ml streptomycin.

In a preliminary experiment air sacs were fixed on slides, stained with Wright's stain and examined microscopically. Although counts of granulocytes by this method were unreliable, there appeared to be significantly fewer residual SCP⁻ than wild type streptococci in fixed tissue. Additional experiments were performed in an attempt to measure this difference. Dispersed cell populations of air sacs were prepared by grinding the air sac in PBS and passing them through Nylon monofilament mesh (TETKO Co. New York).

The cells were pelleted by centrifugation 5 min at 300×g and resuspended at $5\times10^6$/ml in FACS buffer (Hank's balanced salt solution without phenol red, 0.1% $NaN_3$, 1.0% BSA fraction V). Cells ($1.0\times10^6$) were stained directly with 1 $\mu$g FITC anti-mouse Mac-1 or indirectly with 1 $\mu$g Biotin conjugated anti-mouse Gr-1 followed by 1 $\mu$g Streptavidin labelled with fluorescene or FITC. Monoclonal antibodies, Mac-1 and Gr-1, were obtained from Pharmingen, Inc. CA. Labeled cells were fixed in 1.0% paraformaldehyde. Fluorescence profiles were generated using a FAC-Scan flow-cytometer and Consort 32 software (Becton Dickinson). Mouse PMNs were purified from whole blood by Ficoll Hypaque density gradient centrifugation and used as a standard to defined PMNs in mixed populations. For measurement of specifically labeled cells, the mean fluorescence for each antibody marker was determined and gates were set to reflect intensely labeled cells. Controls included unstained cells, and cells exposed to only streptavidin FITC.

Two experiments were performed. The first compared the scpA49 insertion mutant M16 to its SCP⁻ parent culture, strain CS101. The second compared the scpA49 deletion mutant MJ3-15, to its parent, strain CS101Sm. (Table 1) In both experiments homogenized air sacs from mice inoculated with SCP⁻ streptococci contained fewer numbers of streptococci after 4 hours than air sacs inoculated with wild type streptococci. The first experiment showed a two-fold reduction and the second showed a four-fold reduction. These differences were statistically significant at P<0.05 and P<0.001, respectively, using an Unpaired t-test. It was also observed that wild type SCP⁺ streptococci were found in spleen homogenates from 7 of 8 mice and 6 of 8 mice; whereas, the SCP⁻ mutants were rarely found in the spleen. The opposite was true for lymph node homogenates. Nodes from 10 of 16 mice infected with SCP⁻ streptococci harbored viable streptococci; whereas, only 4 of 16 nodes from mice infected with wild type streptococci contained viable bacteria. This difference was determined to be statistically significant at P<0.05 using the Fisher's exact test.

TABLE 1

Distribution of SCP⁺ and SCP⁻ streptococci 4 hours after air sac infection

| Strains | No. of Mice[a] | No. of positive cultures | | Homogenized Air Sac[c] |
|---|---|---|---|---|
| | | spleen[b] | lymph node | |
| CS101pG (SCP⁺) | 8 | 7 | 2 | $1.3 \times 10^8 \pm 2.2 \times 10^7$ |
| M16 (SCP⁻) | 8 | 0 | 5 | $6.0 \times 10^7 \pm 1.3 \times 10^7$ |
| CS101Sm (SCP⁺) | 8 | 6 | 2 | $1.6 \times 10^8 \pm 2.6 \times 10^7$ |
| MJ3-15 (SCP⁻) | 8 | 1 | 5 | $3.7 \times 10^7 \pm 1.5 \times 10^7$ |

[a]Each mouse was inoculated with $3 \times 10^8$ CFU of stationary phase streptococci.
[b]Difference in the frequency of isolation of SCP⁺ streptococci from spleens relative to SCP⁻ streptococci was statistically significant (P < 0.05) for each experiment by the Fisher's exact test.
[c]Differences in CFU isolated from homogenized air sacs (means ± SEMs) were significant, strains CS101pG (SCP⁺) and M16 (SCP⁻) and MJ3-15 (SCP⁻) (P < 0.001) for each experiment by unpaired t test.

The more rapid clearance of streptococci from air sacs resulted from more intense recruitment of PMNs. The total cell population, the percentage of Mac-1 positive granulocytes (Springer, G. et al., "Mac-1:macrophage differentiation antigen identified by monoclonal antibody," *Eur. J. Immunol.* 9:301–306 (1979)), and the percentage of Gr-1 positive PMN (Brummer, E. et al., "Immunological activation of polymorphonuclear neutrophils for fungal killing: studies with murine cells and blastomyces dermatitidis in vitro," *J. Leuko. Bio.* 36:505–520 (1984)) in air sacs were compared by single color FACS analysis. Clark, J. M., "A new method for quantitation of cell-mediated immunity in the mouse," *J. Reticuloendothel. Soc.* 25:255–267 (1979). Briefly, in a FACS analysis, individual cells in suspension are labelled with specific fluorescent monoantibodies. Aliquots of labelled cells are injected into a FAC-Scan flow-cytometer or fluorescent cell sorter which counts cells based on their unique fluorescence.

Figure 4:
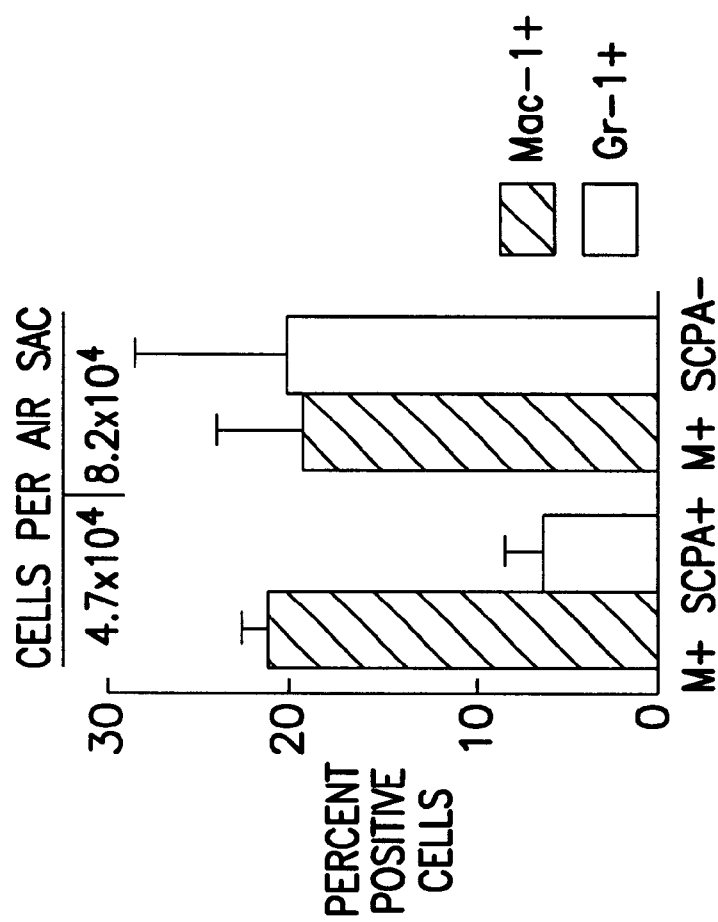
FIG. 4. Single color FACS analysis. Fluorescence data were analyzed by gating on PMNs. A second gate was set to count high staining cells defined by the first gate. Air sacs were inoculated with $1 \times 10^6$ CFU.

Air sacs infected with the SCP⁻ deletion mutant contained twice as many inflammatory cells as those inoculated with SCP⁺ streptococci (FIG. 4). A hundred-fold increase in the inoculum size did not alter this difference. Air sacs infected with $1\times10^6$ SCP⁻ cells, strain MJ3-15, contained three times more Gr-1 positive cells than those inoculated with the SCP⁺ culture. In airs sacs inoculated with SCP⁺ streptococci approximately 6% of the cells were PMNs and 21% were other kinds of Mac-1⁺ granulocytes, including PMNs. In contrast, air sacs inoculated with SCP⁻ streptococci contained predominately PMNs. Gr-1 positive cells were equal to or greater than the number of Mac-1 positive cells. Flow cytometer gates were set to measure only high staining granulocytes. The remaining 70–80% of cells not stained with either antibody were likely either low staining granulocytes, red blood cells or lymphocytes. Large numbers of lymphocytes were observed microscopically in Wrights stained air sac preparations.

SCP⁺ colonies of streptococci that emerged from spleen homogenates were highly encapsulated, resembling water drops. In contrast the few SCP⁻ colonies arising from lymph nodes, were more like the inoculum. They were mixtures of non-mucoid and moderately mucoid colonies. These data suggest that M+SCP+ encapsulated streptococci can adapt, multiply and invade the bloodstream within 4 hours after infection. The basis for differential trafficking of mutant and wild type streptococci may be due to the more vigorous influx of phagocytic cells in response to SCP− bacteria. Macrophages and/or skin dendritic cells may more rapidly engulfed SCP streptococci and delivered them to lymph nodes. Reduction of mutant streptococci relative to wild type is an unexpected finding, because SCP− streptococci are M+ and resistant to phagocytosis by human neutrophils in vitro.

EXAMPLE 3

SCP is Required for Colonization of the Mouse Nasopharynx

Mice were inoculated intranasally to evaluate the relative capacity of wild type (SCP+) and SCP− streptococci to colonize the nasopharynx. Streptomycin resistant M49 strain CS101 and deletion mutant MJ3-15 were used in these experiments. Cultures were not mouse passed in order to avoid selection of variants that might be uniquely mouse virulent, but no longer depend on M protein and/or SCP for persistence in the animal.

Figure 5:
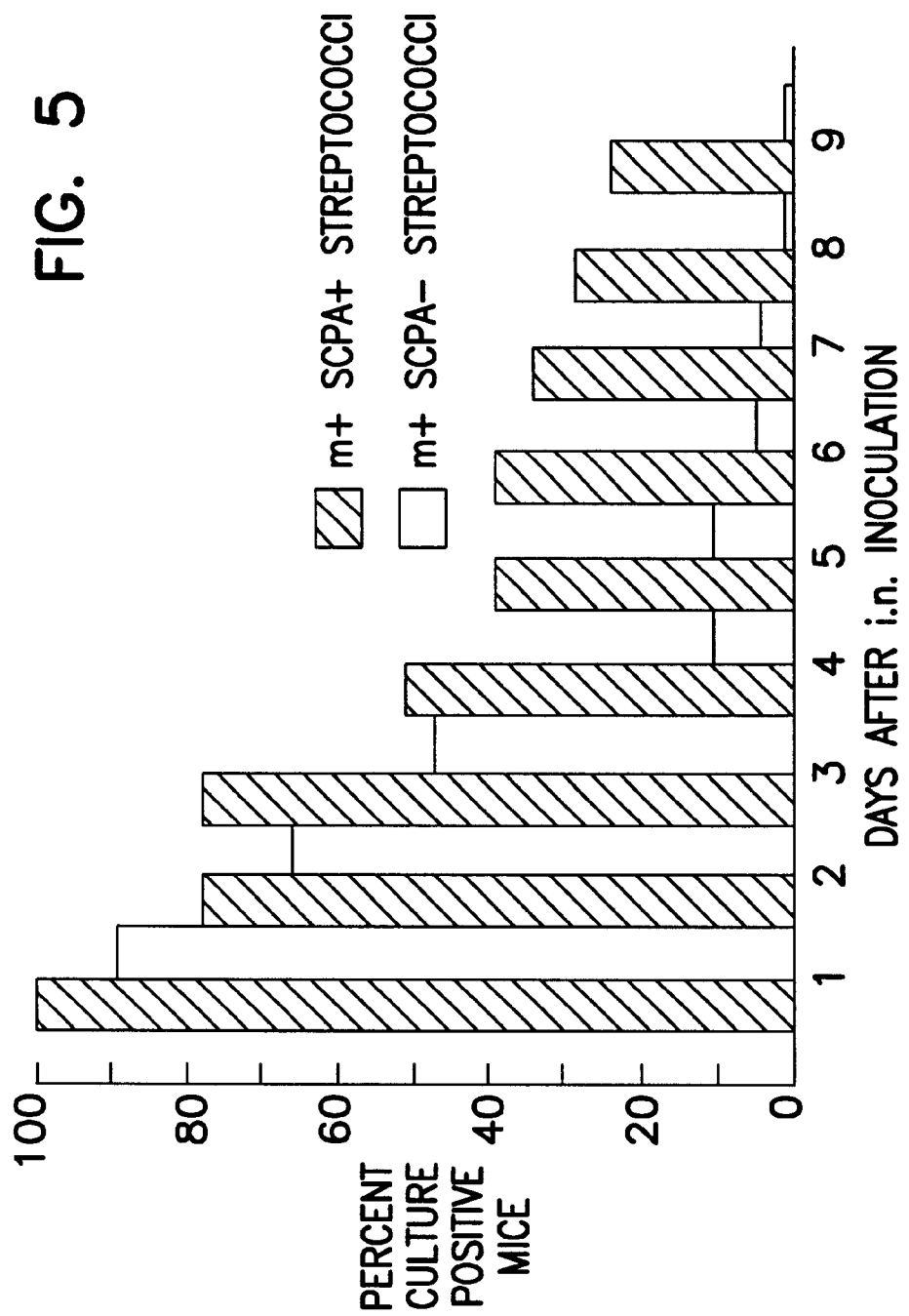
FIG. 5. Persistence of Wild type and SCPA⁻ following intranasal infection.

CD1 outbred mice were intranasally inoculated with $2 \times 10^8$ stationary phase CFU. The nasopharynxes of anesthetized mice were swabbed daily for 8–10 days and streaked on blood agar containing streptomycin. Differences between SCP+ and SCP− were evident by day 1, however, statistically significant differences were not observed until days 3 and 4 (FIG. 5). By day four 9/18 mice infected with M+SCP+ streptococci produced positive throat cultures, whereas only 2/18 mice infected with M+SCP− strain retained streptococci in their throats. Four of 18 mice died from infection with SCP+ streptococci. None of the mice following infection with SCP− bacteria succumbed to the infection. The numbers of colonies on the blood agar plates were also consistent with more rapid clearance of SCP− streptococci. For example, on the third day cultures from seven mice contained >100 SCP+ CFU, whereas, only one mouse inoculated SCP− streptococci contained >100 CFU.

Because M49 streptococci are more often associated with skin infections the above experiments were repeated with an M6 strain, a serotype more often associated with throat infections. An insertion mutant, strain AK1.4, was constructed using the M6 strain UAB200 and the strategy previously described in Example 1. Strain AK1.4 was also cleared more rapidly than the wild type M6 culture from the nasopharynx. The above experiments confirm that group A streptococci are dependent upon SCP for persistence in the mouse nasopharynx. All SCP− mutants used in the above experiments were M+, i.e. they resisted phagocytosis by fresh human blood. Yet, they were cleared from the nasopharyngeal mucosa.

EXAMPLE 4

Intranasal Immunization of Mice with Purified Recombinant SCPA49 Blocks Colonization Following Intranasal Challenge A PCR fragment which corresponds to a deleted form of the scpA49 gene was cloned from CS101 M49 group A streptococci (dSCP). This fragment was amplified by PCR using a forward primer beginning at nucleotide 1033 and a reverse primer beginning at nucleotide 3941 (numbering corresponding to that of Chen, C., and Cleary, P., "Complete nucleotide sequence of the streptococcal C5a peptidase gene of Streptococcus pyogenes," *J. Biol. Chem.*, 265:3161–3167 (1990)). The fragment was ligated to the thrombin binding site of glutathione transferase gene on the pGex-4T-1 high expression vector from Pharmacia Inc. The plasmid containing scpA designated pJC6 has been deposited in the American Type Culture Collection, Rockville, Md., under the provision of the Budapest Treaty, and assigned ATCC accession number 98225.

The transferase-SCP fusion protein from one *E. coli* clone was expressed and purified by affinity chromatography on a glutathione Sepharose 4b column. All methods are described by the manufacturer (Pharmacia). The dSCP was cleaved from the hybrid protein by thrombin digestion. The thrombin was removed from eluted SCP by chromatography on a benzamidine Sepharose 6B column (Pharmacia). The affinity purified protein was confirmed to be pure SCPA49 by SDS-PAGE and by Western blot. Hyperimmune antiserum, directed against purified SCPA49 was prepared in rabbits. The recombinant SCP was not functional as a peptidase.

Two groups of mice were immunized by administration of $10\,\mu l$ into each nostril, a total of $40\,\mu g$ of protein, four times over a period of five weeks. Control mice received only PBS. Prior to infection sera pooled from groups of 5 mice were determined by ELISA to have high titers of anti-SCPA49 antibody. See Table 2.

TABLE 2

Titers of antibodies (IgG) against SCP

| Exp | Sample | Before Immunization | After Immunization |
|---|---|---|---|
| I | pool I | <1:10 | 1:320–1:640 |
| ScP | pool II | <1:10 | 1:320 |
|  | pool III | <1:10 | 1:640–1:1,280 |
| I | pool I | <1:10 | <1:10 |
| PBS | pool II | <1:10 | <1:10 |
|  | pool III | <1:10 | <1.10 |
| II | pool I | <1:10 | 1:5,120 |
| PBS | pool II | <1:10 | 1:2,560 |
|  | pool III | <1:10 | 1:5,120 |
| II | pool I | <1:10 | <1:10 |
| PBS | pool II | <1:10 | <1:10 |
|  | pool III | <1:10 | <1:10 |
| III | pool I | <1:10 | 1:800 |
| SCP | pool II | <1:10 | 1:800 |
| III PBS | pool I | <1:10 | <1:10 |

Figure 6B:
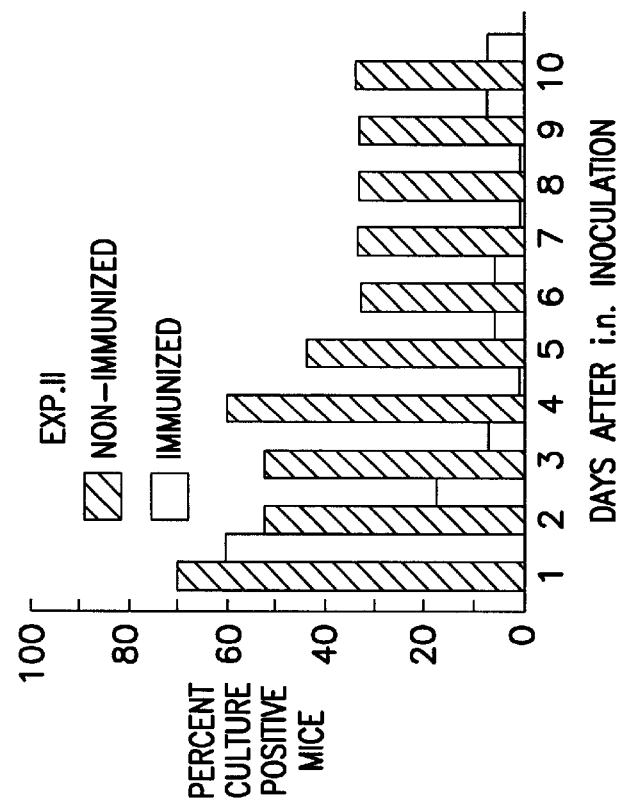
FIG. 6. Intranasal immunization of CD-1 mice with SPCA protein interferes with oral colonization by M type 49 streptococci.
Figure 6A:
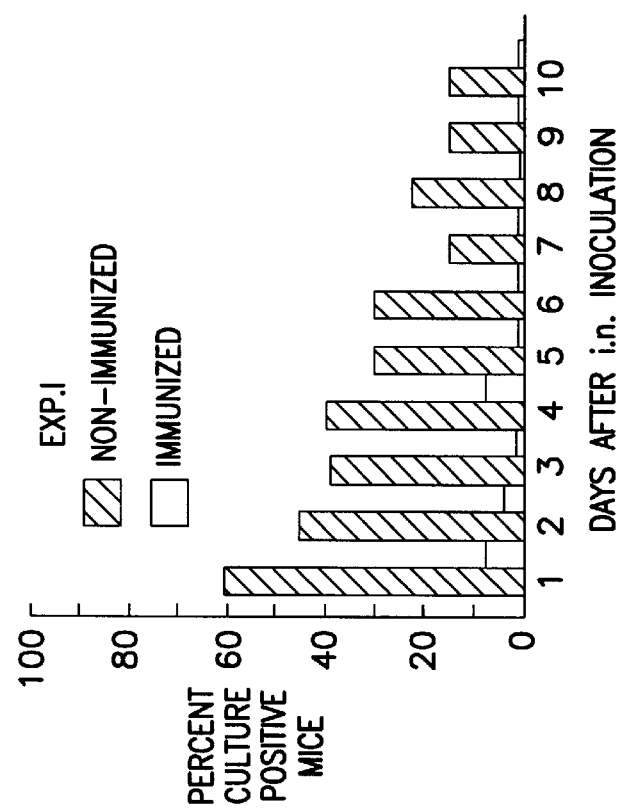

Mice were challenged with $3 \times 10^8$ CFU of the wild type, CS101sm strain, 7 days after the last vaccine booster. In two separate experiments immunized mice were free of streptococci 48 hrs after infection (FIG. 6; Tables 3 and 4). In contrast 30–50% of non-vaccinated controls remained culture positive for six days, and some were still positive ten days after infection. Differences were determined to be statistically significant by the Fisher exact test. Infection of a third group of immunized and control mice produced similar results.

High titer rabbit serum directed against this mutant SCPA49 protein was able to neutralize peptidase activity associated with intact M1, M12, and M6 streptococci in vitro, confirming that peptidase lacks serotype specificity. Therefore, even SCP which is not functional as a peptidase is effective as a vaccine. It should be noted that pre-incubation of M49 streptococci with rabbit anti-SCP prior to in. inoculation of mice did not reduce colonization.

TABLE 3

Throat cultures for *streptococci* after intranasal challenge of mice vaccinated intranasally with PBS or SCP expressed in *E. coli* DH5α (CFU after vaccine)

| | Days after challenge | | | | | | | | | |
|---|---|---|---|---|---|---|---|---|---|---|
| Mice | 1 | 2 | 3 | 4 | 5 | 6 | 7 | 8 | 9 | 10 |
| PBSCT-II | | | | | | | | | | |
| 1 | 0 | 0 | 0 | 0 | 0 | 0 | 0 | 0 | 0 | 0 |
| 2 | 3 | 0 | 0 | 0 | 0 | 0 | 0 | 0 | 0 | 0 |
| 3 | 77 | >200 | 150 | 4 | 11 | 3 | 0 | 51 | 97 | 53 |
| 4 | 9 | >200 | >200 | 3 | 11 | 3 | 0 | 0 | 0 | 0 |
| 5 | 0 | 0 | 0 | 0 | 0 | 0 | 0 | 0 | 0 | 0 |
| 6 | 4 | 6 | 45 | 47 | 3 | >200 | 29 | >200 | 83 | 70 |
| 7 | 15 | 194 | >200 | 9 | 172 | 10 | 5 | 3 | 0 | 0 |
| 8 | 0 | 0 | 0 | 0 | 0 | 0 | 0 | 0 | 0 | 0 |
| 9 | 0 | 32 | 4 | 4 | 0 | 0 | 0 | 0 | 0 | 0 |
| 10 | 2 | 0 | 0 | 0 | 0 | 0 | 0 | 0 | 0 | 0 |
| 11 | 3 | 0 | 0 | 0 | 0 | 0 | 0 | 0 | 0 | 0 |
| 12 | 0 | 0 | 0 | 0 | 0 | 0 | 0 | 0 | 0 | 0 |
| 13 | 127 | 4 | 0 | 0 | 0 | 0 | 0 | 0 | 0 | 0 |

TABLE 3-continued

Throat cultures for *streptococci* after intranasal challenge of mice vaccinated intranasally with PBS or SCP expressed in *E. coli* DH5α (CFU after vaccine)

| | Days after challenge | | | | | | | | | |
|---|---|---|---|---|---|---|---|---|---|---|
| Mice | 1 | 2 | 3 | 4 | 5 | 6 | 7 | 8 | 9 | 10 |
| No. of positive | 8 | 6 | 5 | 5 | 4 | 4 | 2 | 3 | 2 | 2 |
| SCP-AD-II | | | | | | | | | | |
| 1 | 0 | 0 | 0 | 0 | 0 | 0 | 0 | 0 | 0 | 0 |
| 2 | 0 | 0 | 0 | 0 | 0 | 0 | 0 | 0 | 0 | 0 |
| 3 | 0 | 0 | 0 | 0 | 0 | 0 | 0 | 0 | 0 | 0 |
| 4 | 0 | 0 | 0 | 0 | 0 | 0 | 0 | 0 | 0 | 0 |
| 5 | 35 | 0 | 0 | 0 | 0 | 0 | 0 | 0 | 0 | 0 |
| 6 | 0 | 0 | 0 | 0 | 0 | 0 | 0 | 0 | 0 | 0 |
| 7 | 0 | 0 | 0 | 0 | 0 | 0 | 0 | 0 | 0 | 0 |
| 8 | 0 | 0 | 0 | 0 | 0 | 0 | 0 | 0 | 0 | 0 |
| 9 | 0 | 0 | 0 | 0 | 0 | 0 | 0 | 0 | 0 | 0 |
| 10 | 0 | 0 | 0 | 0 | 0 | 0 | 0 | 0 | 0 | |
| 11 | 0 | 0 | 0 | 21 | 0 | 0 | 0 | 0 | 0 | 0 |
| 12 | 0 | 0 | 0 | 0 | 0 | 0 | 0 | 0 | 0 | 0 |
| 13 | 0 | 0 | 0 | 0 | 0 | 0 | 0 | 0 | 0 | 0 |
| No. of positive | 1 | 0 | 0 | 1 | 0 | 0 | 0 | 0 | 0 | 0 |

TABLE 4

Throat cultures for *streptococci* after intranasal challenge of mice vaccinated intranasally with PBS or SCP expressed in *E. coli* DH5α (CFU after vaccine)

| | Days after challenge | | | | | | | | | |
|---|---|---|---|---|---|---|---|---|---|---|
| Mice* | 1 | 2 | 3 | 4 | 5 | 6 | 7 | 8 | 9 | 10 |
| PBSCT-I | | | | | | | | | | |
| 1 | 112 | 143 | 85 | 16 | 0 | 0 | 0 | 0 | 0 | 0 |
| 2 | 127 | 27 | 18 | 89 | 3 | 7 | 7 | 7 | 70 | 3 |
| 3 | >200 | >200 | >200 | >200 | >200 | >200 | >200 | 108 | >200 | 66 |
| 4 | 31 | 200 | 4 | 2 | 0 | 0 | 0 | 0 | 0 | 0 |
| 5 | 4 | 0 | 0 | 3 | 3 | 0 | 0 | 0 | 0 | 0 |
| 6 | 0 | 0 | 0 | 0 | 0 | 0 | 0 | 0 | 0 | 0 |
| 7 | >200 | >200 | 120 | 125 | 91 | 145 | >200 | >200 | >200 | 166 |
| 8 | 2 | 0 | 0 | 0 | 0 | 0 | 0 | 0 | 0 | 0 |
| 9 | 0 | 0 | 0 | 0 | 0 | 0 | 0 | 0 | 0 | 0 |
| 10 | 0 | 0 | 0 | 0 | 0 | 0 | 0 | 0 | 0 | 0 |
| 11 | 37 | >200 | 194 | 16 | >200 | 47 | >200 | 101 | >200 | >200 |
| No. of positive | 8 | 6 | 6 | 7 | 5 | 4 | 4 | 4 | 4 | 4 |
| SCPAD-I | | | | | | | | | | |
| 1 | 6 | 0 | 0 | 0 | 0 | 0 | 0 | 0 | 0 | 0 |
| 2 | 105 | 41 | 0 | 0 | 0 | 0 | 0 | 0 | 0 | 0 |
| 3 | 0 | 0 | 0 | 0 | 0 | 0 | 0 | 0 | 0 | 0 |
| 4 | 2 | 0 | 0 | 0 | 0 | 0 | 0 | 0 | 0 | 0 |
| 5 | 2 | 0 | 0 | 0 | 0 | 0 | 0 | 0 | 0 | 0 |
| 6 | 9 | 0 | 11 | 0 | 0 | 0 | 0 | 0 | 0 | 0 |
| 7 | 0 | 0 | 0 | 0 | 0 | 0 | 0 | 0 | 0 | 0 |
| 8 | 26 | 0 | 0 | 0 | 0 | 0 | 0 | 0 | 0 | 0 |
| 9 | 0 | 19 | 0 | 0 | 5 | 57 | 0 | 0 | 21 | 91 |
| 10 | 0 | 0 | 0 | 0 | 0 | 0 | 0 | 0 | 0 | 0 |
| 11 | 7 | 0 | 0 | 0 | 0 | 0 | 0 | 0 | 0 | 0 |
| No. of positive | 7 | 2 | 1 | 0 | 1 | 1 | 0 | 0 | 1 | 1 |

*Mice were inoculated twice, because the dose of bacteria was too low at first time inoculation.

EXAMPLE 5

C5a Peptidase from Group B Streptococci is Nearly Identical in Sequence to those from M12 and M49 Group A Streptococci The group B streptococci C5a peptidase (SCPB) gene was cloned, sequenced and compared to that from serotype group A streptococci M12 and M49. The entire scpB gene was amplified by PCR using primers which correspond to portions of the scpA12 sequence using the method described in Example 4 above. The SCPB gene encodes an open reading frame (ORF) of 3450 bp which specifies a protein of 1150 amino acids with Mr of 126,237da. The amino acid sequence of SCPB is shown in FIG. 2. Comparison of the scpB nucleotide and deduced amino acid sequence to those from M12 and M49 group A streptococci showed high similarities, 98% and 97%, respectively. scpB contained a 50 bp deletion which overlapped two of the C-terminal repeats, and had several other minor differences relative to scpA genes. Alignment of the sequences showed that scpA12 is actually phylogenetically closer to scpB than it is to scpA49. Thirty strains, representing serotypes III, III/R, II, Ia/c, NT/c, NT/c/R1 carry a copy of scpB.

Recombinant SCP was expressed in *E. coli* using expression vector plasmid pGEX-4T-1 (ATCC accession number 98225) and was shown to be identical to the enzyme extracted from the parental group B streptococcal strain 78-471 (Type II a+b). Western blot analysis suggested the recombinant SCP is identical to the C5ase enzyme previously purified from group B streptococci.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

---

What is claimed is:

1. A vaccine comprising an immunogenic amount of an enzymatically inactive streptococcal C5a peptidase (SCP) peptide, wherein the peptide comprises the catalytic domain of SCP, which amount is effective to prevent or ameliorate β-hemolytic Streptococcus colonization or infection in a susceptible mammal in combination with a physiologically-acceptable, non-toxic vehicle.

2. The vaccine of claim 1 which further comprises an effective amount of an immunological adjuvant.

3. The vaccine of claim 1 wherein the mammal is a human, dog, bovine, porcine or horse.

4. The vaccine of claim 3 wherein the mammal is human.

5. The vaccine of claim 1 wherein the β-hemolytic Streptococcus is group A Streptococcus, group B Streptococcus, group C Streptococcus or group G Streptococcus.

6. A method according to claim 5, wherein the β-hemolytic Streptococcus is Group A Streptococcus.

7. The vaccine of claim 1, which comprises an enzymatically inactive streptococcal C5a peptidase, conjugated or linked to a peptide.

8. The vaccine of claim 1, which comprises an enzymatically inactive streptococcal C5a peptidase, conjugated or linked to a polysaccharide.

9. A method of protecting a susceptible mammal against β-hemolytic Streptococcus colonization or infection comprising administering to the mammal an effective amount of a vaccine comprising an immunogenic amount of an enzymatically inactive streptococcal C5a peptidase (SCP) peptide, wherein the peptide includes the catalytic domain of SCP, which amount is effective to prevent or ameliorate Streptococcus colonization or infection in the susceptible mammal in combination with a physiologically-acceptable, non-toxic vehicle.

10. The method of claim 9 wherein the vaccine further comprises an effective amount of an immunological adjuvant.

11. The method of claim 9 wherein the vaccine is administered by subcutaneous or intramuscular injection.

12. The method of claim 9 wherein the vaccine is administered by oral ingestion.

13. The method of claim 9 wherein the vaccine is administered intranasally.

14. A method according to claim 9, wherein the β-hemolytic Streptococcus is group A Streptococcus, group B Streptococcus, group C Streptococcus or group G Streptococcus.

15. A method according to claim 14, wherein the β-hemolytic Streptococcus is group A Streptococcus.

16. The method according to claim 9 wherein the mammal is a human, dog, bovine, porcine, or horse.

17. The method according to claim 16 wherein the mammal is human.

18. The method of claim 9, wherein the vaccine comprises an enzymatically inactive streptococcal C5a peptidase, conjugated or linked to a peptide.

19. The method of claim 9, wherein the vaccine comprises an enzymatically inactive C5a peptidase, conjugated or linked to a polysaccharide.

20. The vaccine of claim 1, wherein the catalytic domain is the sequence corresponding essentially to amino acid residue 130 to amino acid residue 512 of SEQ ID NO:1, SEQ ID NO:2 or SEQ ID NO:3.

21. The vaccine of claim 1, wherein the catalytic domain corresponds to SEQ ID NO:6, SEQ ID NO:7 or SEQ ID NO:8.

22. The vaccine of claim 1, wherein the enzymatically inactive peptide further comprises the region of SCP between the catalytic domain and the cell wall insert.

23. The vaccine of claim 22, wherein the enzymatically inactive peptide is the sequence corresponding essentially to amino acid residue 130 to amino acid residue 1050 of SEQ ID NO:1, SEQ ID NO:2 or SEQ ID NO:3.

24. The vaccine of claim 22, wherein the enzymatically inactive peptide corresponds to SEQ ID NO:9, SEQ ID NO:10 or SEQ ID NO:11.

25. A vaccine comprising an immunogenic amount of an enzymatically inactive peptide comprising the catalytic domain of streptococcal C5a peptidase (SCP), wherein the peptide is capable of generating antibody specifically recognizes a streptococcal C5a peptidase (SCP), and wherein the amount is effective to prevent or ameliorate β-hemolytic Streptococcus colonization or infection in a susceptible mammal in combination with a physiologically-acceptable, non-toxic vehicle.

26. The vaccine of claim 25, wherein the catalytic domain is the sequence corresponding essentially to amino acid residue 130 to amino acid residue 512 of SEQ ID NO:1, SEQ ID NO:2 or SEQ ID NO:3.

27. The vaccine of claim 25, wherein the catalytic domain corresponds to SEQ ID NO:6, SEQ ID NO:7 or SEQ ID NO:8.

28. The vaccine of claim 25, wherein the enzymatically inactive peptide further comprises the region of SCP between the catalytic domain and the cell wall insert.

29. The vaccine of claim 28, wherein the enzymatically inactive peptide is the sequence corresponding essentially to amino acid residue 130 to amino acid residue 1050 of SEQ ID NO:1, SEQ ID NO:2 or SEQ ID NO:3.

30. The vaccine of claim 28, wherein the enzymatically inactive peptide corresponds to SEQ ID NO:9, SEQ ID NO:10 or SEQ ID NO:11.

31. The method of claim 9, wherein the catalytic domain is the sequence corresponding essentially to amino acid residue 130 to amino acid residue 512 of SEQ ID NO:1, SEQ ID NO:2 or SEQ ID NO:3.

32. The method of claim 9, wherein the catalytic domain corresponds to SEQ ID NO:6, SEQ ID NO:7 or SEQ ID NO:8.

33. The method of claim 9, wherein the enzymatically inactive peptide further comprises the region of SCP between the catalytic domain and the cell wall insert.

34. The method of claim 33, wherein the enzymatically inactive peptide is the sequence corresponding essentially to amino acid residue 130 to amino acid residue 1050 of SEQ ID NO:1, SEQ ID NO:2 or SEQ ID NO:3.

35. The method of claim 33, wherein the enzymatically inactive peptide corresponds to SEQ ID NO:9, SEQ ID NO:10 or SEQ ID NO:11.

36. A method of protecting a susceptible mammal against β-hemolytic Streptococcus colonization or infection comprising administering to the mammal an effective amount of vaccine comprising an immunogenic amount of an enzymatically inactive peptide comprising the catalytic domain of streptococcal C5a peptidase (SCP), wherein the peptide is capable of generating antibody specific to streptococcal C5a peptidase (SCP), and wherein the amount is effective to prevent or ameliorate β-hemolytic Streptococcus colonization or infection in a susceptible mammal in combination with a physiologically-acceptable, non-toxic vehicle.

37. The method of claim 36, wherein the catalytic domain is the sequence corresponding essentially to amino acid residue 130 to amino acid residue 512 of SEQ ID NO:1, SEQ ID NO:2 or SEQ ID NO:3.

38. The method of claim 36, wherein the catalytic domain corresponds to SEQ ID NO:6, SEQ ID NO:7 or SEQ ID NO:8.

39. The method of claim 36, wherein the enzymatically inactive peptide further comprises the region of SCP between the catalytic domain and the cell wall insert.

40. The method of claim 39 wherein the enzymatically inactive peptide is the sequence corresponding essentially to amino acid residue 130 to amino acid residue 1050 of SEQ ID NO:1, SEQ ID NO:2 or SEQ ID NO:3.

41. The method of claim 39, wherein the enzymatically inactive peptide corresponds to SEQ ID NO:9, SEQ ID NO:10 or SEQ ID NO:11.

42. A vaccine comprising an immunogenic amount of an enzymatically inactive peptide comprising an epitope of the catalytic domain of streptococcal C5a peptidase (SCP), wherein the peptide is capable of generating antibody that specifically recognizes a streptococcal C5a peptidase (SCP), and wherein the amount is effective to prevent or ameliorate β-hemolytic Streptococcus colonization or infection in a susceptible mammal in combination with a physiologically-acceptable, non-toxic vehicle.

\* \* \* \* \*